(12) United States Patent
Moon et al.

(10) Patent No.: US 11,363,959 B2
(45) Date of Patent: Jun. 21, 2022

(54) BIO-SIGNAL MEASURING APPARATUS AND OPERATING METHOD THEREOF

(71) Applicant: SAMSUNG ELECTRONICS CO., LTD., Suwon-si (KR)

(72) Inventors: Hyun Seok Moon, Seoul (KR); Seung Jun Lee, Seoul (KR); Jae Wook Shim, Yongin-si (KR); Hyeong Seok Jang, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 331 days.

(21) Appl. No.: 16/228,914

(22) Filed: Dec. 21, 2018

(65) Prior Publication Data
US 2019/0200883 A1    Jul. 4, 2019

(30) Foreign Application Priority Data
Dec. 29, 2017    (KR) .................... 10-2017-0183327

(51) Int. Cl.
*A61B 5/026*     (2006.01)
*A61B 5/0531*    (2021.01)
*A61B 5/024*     (2006.01)
*A61B 5/02*      (2006.01)
(Continued)

(52) U.S. Cl.
CPC ........ *A61B 5/0261* (2013.01); *A61B 5/02416* (2013.01); *A61B 5/0531* (2013.01); *A61B 5/30* (2021.01); *A61B 5/6843* (2013.01); *A61B 5/02007* (2013.01)

(58) Field of Classification Search
CPC .. A61B 5/02007–02035; A61B 5/0205; A61B 5/021–02141; A61B 5/024–02444; A61B 5/0255; A61B 5/026–0261; A61B 5/14546; A61B 5/1455–14552; A61B 5/14557; A61B 5/1477; A61B 5/14532; A61B 5/25; A61B 5/256;
(Continued)

(56) References Cited

U.S. PATENT DOCUMENTS

| 6,696,428 | B2 | 2/2004 | Nickel et al. |
| 7,474,917 | B2 | 1/2009 | Jang et al. |
| 8,148,686 | B2 | 4/2012 | Ryhänen et al. |

(Continued)

FOREIGN PATENT DOCUMENTS

| JP | 2005-270546 A | 10/2005 |
| KR | 10-1692004 B1 | 1/2017 |
| WO | 2017182677 A2 | 10/2017 |

OTHER PUBLICATIONS

Communication dated May 2, 2019, issued by the European Patent Office in counterpart European Application No. 18248149.9.

*Primary Examiner* — Thaddeus B Cox
(74) *Attorney, Agent, or Firm* — Sughrue Mion, PLLC

(57) ABSTRACT

A bio-signal measuring apparatus includes an optical sensor including a photodetector and a light source array disposed around the photodetector, a first electrode disposed between the photodetector and the light source array, and a second electrode disposed on an outer periphery of the light source array. The bio-signal measuring apparatus further includes an impedance measurer configured to measure an impedance of an object, using the first electrode and the second electrode, and a processor configured to determine a contact state between the object and the optical sensor, based on the measured impedance.

18 Claims, 25 Drawing Sheets

(51) Int. Cl.
*A61B 5/00* (2006.01)
*A61B 5/30* (2021.01)

(58) Field of Classification Search
CPC ....... A61B 5/02416–0261; A61B 5/053–0533; A61B 5/6843
See application file for complete search history.

(56) References Cited

U.S. PATENT DOCUMENTS

| | | |
|---|---|---|
| 9,060,700 B2 | 6/2015 | Cho et al. |
| 2006/0009698 A1* | 1/2006 | Banet ................ G06F 19/00 600/485 |
| 2008/0171922 A1 | 7/2008 | Teller et al. |
| 2009/0174671 A1* | 7/2009 | Tachi ................ G06F 3/016 345/173 |
| 2010/0022861 A1* | 1/2010 | Cinbis ............... A61B 5/0084 600/325 |
| 2011/0019373 A1 | 1/2011 | Ryhanen et al. |
| 2012/0016210 A1 | 1/2012 | Kim et al. |
| 2013/0274841 A1* | 10/2013 | Eckhous ............ A61B 18/14 607/101 |
| 2015/0109617 A1* | 4/2015 | Gilbert .............. G01J 3/42 356/300 |
| 2016/0324440 A1 | 11/2016 | Kim et al. |
| 2017/0105646 A1 | 4/2017 | Bryenton et al. |
| 2017/0164878 A1* | 6/2017 | Connor ............. A61B 5/053 |
| 2017/0366213 A1* | 12/2017 | Camacho Perez .... A61B 5/389 |
| 2018/0064395 A1* | 3/2018 | Shim ................. A61B 5/0004 |
| 2019/0059821 A1 | 2/2019 | Pekonen et al. |
| 2020/0233381 A1* | 7/2020 | Yang ................. H05K 1/0277 |

\* cited by examiner

BIO-SIGNAL MEASURING APPARATUS AND OPERATING METHOD THEREOF

CROSS-REFERENCE TO RELATED APPLICATION

This application claims priority from Korean Patent Application No. 10-2017-0183327, filed on Dec. 29, 2017, in the Korean Intellectual Property Office, the disclosure of which is incorporated herein by reference in its entirety.

BACKGROUND

1. Field

Apparatuses and methods consistent with embodiments relate to a bio-signal measuring apparatus and an operating method thereof.

2. Description of the Related Art

With the increasing interest in health, various bio-signal measuring techniques have been developed recently. For example, even a wearable device worn by a user has a sensor for measuring a bio-signal, so that the user may measure their bio-signal by using the sensor embedded in the wearable device. Depending on the types of object to be analyzed, or the purpose of measurement, the user may temporarily measure the bio-signal, or may continuously measure the bio-signal for a predetermined period of time. The bio-signal obtained in this manner may be used alone, or in combination with other bio-signals, as an indicator of a user's health.

A measurement position, a measurement condition, and the like may be continuously changed according to a user's movement and the like, such that the sensor for measuring a bio-signal ensures accuracy and reproducibility of measurement. In the case of measurement using an optical sensor, an optical signal measured by the optical sensor is prone to have noise depending on a contact state between the optical sensor and the object, such that the contact state may significantly affect the accuracy or reproducibility of measurement.

SUMMARY

According to embodiments, there is provided a bio-signal measuring apparatus, including an optical sensor including a photodetector and a light source array disposed around the photodetector, a first electrode disposed between the photodetector and the light source array, and a second electrode disposed on an outer periphery of the light source array. The bio-signal measuring apparatus further includes an impedance measurer configured to measure an impedance of an object, using the first electrode and the second electrode, and a processor configured to determine a contact state between the object and the optical sensor, based on the measured impedance.

Each of the first electrode and the second electrode may have a ring shape.

Each of the first electrode and the second electrode may have a concentric ring shape.

The impedance measurer may be further configured to apply a current to the object, through the first electrode and the second electrode, measure a voltage that is generated between the first electrode and the second electrode through which the current is applied to the object, and obtain the impedance, based on the applied current and the measured voltage.

The processor may be further configured to compare the measured impedance with a predetermined threshold value, and determine the contact state, based on a result of the measured impedance being compared with the predetermined threshold value.

The processor may be further configured to, based on the measured impedance being compared to be less than or equal to the predetermined threshold value, determine that the contact state is good.

The optical sensor may be configured to measure an optical signal, and the processor may be further configured to, based on the contact state being determined to be good, estimate bio-information of the object, using the measured optical signal.

The bio-information may include any one or any combination of a blood pressure, a vascular age, a degree of arteriosclerosis, a cardiac output, a vascular compliance, a blood glucose, a triglyceride, a cholesterol, a protein, an uric acid, and a peripheral vascular resistance.

The processor may be further configured to, based on the measured impedance being compared to be greater than the predetermined threshold value, determine that the contact state is poor.

The optical sensor may configured to measure an optical signal, and the processor may be further configured to, based on the contact state being determined to be poor, perform any one or any combination of controlling the optical sensor to stop measuring the optical signal, ignoring the measured optical signal, correcting the measured optical signal, and generating an alarm or guide information for improving the contact state.

According to embodiments, there is provided a bio-signal measuring apparatus, including an optical sensor including a photodetector and a light source array disposed around the photodetector, a first electrode disposed between the photodetector and the light source array, and a second electrode array disposed around the light source array, wherein the second electrode array includes a plurality of electrodes. The bio-signal measuring apparatus further includes an impedance measurer configured to measure an impedance of an object for each of the plurality of electrodes, using the first electrode and the second electrode array, and a processor configured to determine a contact state between the object and the optical sensor and a location of a contact failure between the object and the optical sensor, based on the measured impedance for each of the plurality of electrodes.

Each of the first electrode and the second electrode array may have a ring shape.

Each of the first electrode and the second electrode array may have a concentric ring shape.

The impedance measurer may be further configured to apply a current to the object, through the first electrode and each of the plurality of electrodes, measure a voltage that is generated between the first electrode and each of the plurality of electrodes through which the current is applied to the object, and obtain the impedance for each of the plurality of electrodes, based on the applied current and the measured voltage generated between the first electrode and each of the plurality of electrodes.

The processor may be further configured to compare the measured impedance for each of the plurality of electrodes, with a predetermined threshold value, and determine the contact state and the location of the contact failure, based on a result of the measured impedance for each of the plurality of electrodes being compared with the predetermined threshold value.

The processor may be further configured to, based on the measured impedance for each of the plurality of electrodes being compared to be less than or equal to the predetermined threshold value, determine that the contact state is good.

The optical sensor may be configured to measure an optical signal, and the processor may be further configured to, based on the contact state being determined to be good, estimate bio-information of the object, using the measured optical signal.

The bio-information may include any one or any combination of a blood pressure, a vascular age, a degree of arteriosclerosis, a cardiac output, a vascular compliance, a blood glucose, a triglyceride, a cholesterol, a protein, an uric acid, and a peripheral vascular resistance.

The processor may be further configured to, based on the measured impedance for at least one of the plurality of electrodes being compared to be greater than the predetermined threshold value, determine that the contact state is poor.

The processor may be further configured to determine the location of the contact failure at the at least one of the plurality of electrodes for which the measured impedance is greater than the predetermined threshold value.

The optical sensor may be configured to measure an optical signal, and the processor may be further configured to, based on the contact state being determined to be poor, perform any one or any combination of controlling the optical sensor to stop measuring the optical signal, ignoring the measured optical signal, correcting the measured optical signal, and generating an alarm or guide information for improving the contact state.

According to embodiments, there is provided an operating method of a bio-signal measuring apparatus that includes an optical sensor including a photodetector and a light source array disposed around the photodetector, a first electrode disposed between the photodetector and the light source array, and a second electrode disposed on an outer periphery of the light source array, the method including measuring an impedance of an object, using the first electrode and the second electrode, and determining a contact state between the object and the optical sensor, based on the measured impedance.

The measuring of the impedance may include applying a current to the object, through the first electrode and the second electrode, measuring a voltage that is generated between the first electrode and the second electrode through which the current is applied to the object; and obtaining the impedance, based on the applied current and the measured voltage.

The determining of the contact state may include comparing the measured impedance with a predetermined threshold value, and determining the contact state, based on a result of the measured impedance being compared with the predetermined threshold value.

The determining of the contact state may further include, based on the measured impedance being compared to be less than or equal to the predetermined threshold value, determining that the contact state is good.

The method may further include measuring an optical signal, and based on the contact state being determined to be good, estimating bio-information of the object, using the measured optical signal.

The bio-information may include any one or any combination of a blood pressure, a vascular age, a degree of arteriosclerosis, a cardiac output, a vascular compliance, a blood glucose, a triglyceride, a cholesterol, a protein, an uric acid, and a peripheral vascular resistance.

The determining of the contact state may further include, based on the measured impedance being compared to be greater than the predetermined threshold value, determining that the contact state is poor.

The method may further include measuring an optical signal, and based on the contact state being determined to be poor, performing any one or any combination of controlling the optical sensor to stop measuring the optical signal, ignoring the measured optical signal, correcting the measured optical signal, and generating an alarm or guide information for improving the contact state.

According to embodiments, there is provided an operating method of a bio-signal measuring apparatus that includes an optical sensor including a photodetector and a light source array disposed around the photodetector, a first electrode disposed between the photodetector and the light source array, and a second electrode array disposed around the light source array, the second electrode array including a plurality of electrodes, and the method including measuring an impedance of an object for each of the plurality of electrodes, using the first electrode and the second electrode array, and determining a contact state between the object and the optical sensor and a location of a contact failure between the object and the optical sensor, based on the measured impedance for each of the plurality of electrodes.

According to embodiments, there is provided a bio-signal measuring apparatus, including a photodetector configured to measure an optical signal, a first electrode having a ring shape, and disposed around the photodetector, a light source array having the ring shape, and disposed around the first electrode, and a second electrode having the ring shape, and disposed around the light source array. The bio-signal measuring apparatus further includes an impedance measurer configured to measure, using the first electrode and the second electrode, an impedance of an object on which the bio-signal measuring apparatus is disposed, and a processor configured to determine whether the measured impedance is less than or equal to a predetermined threshold value, and based on the measured impedance being determined to be less than or equal to the predetermined threshold value, estimate bio-information of the object, based on the measured optical signal.

The impedance measurer may include a power source configured to apply a current to the object, through the first electrode and the second electrode, and a voltmeter configured to measure a voltage that is generated between the first electrode and the second electrode through which the current is applied to the object. The impedance measurer may be further configured to obtain the impedance, based on the applied current and the measured voltage.

The processor may be further configured to, based on the measured impedance being determined to be greater than the predetermined threshold value, perform any one or any combination of controlling the photodetector to stop measuring the optical signal, ignoring the measured optical signal, correcting the measured optical signal, and generating an alarm or guide information for improving a contact between the object and the bio-signal measuring apparatus.

Figure 1:
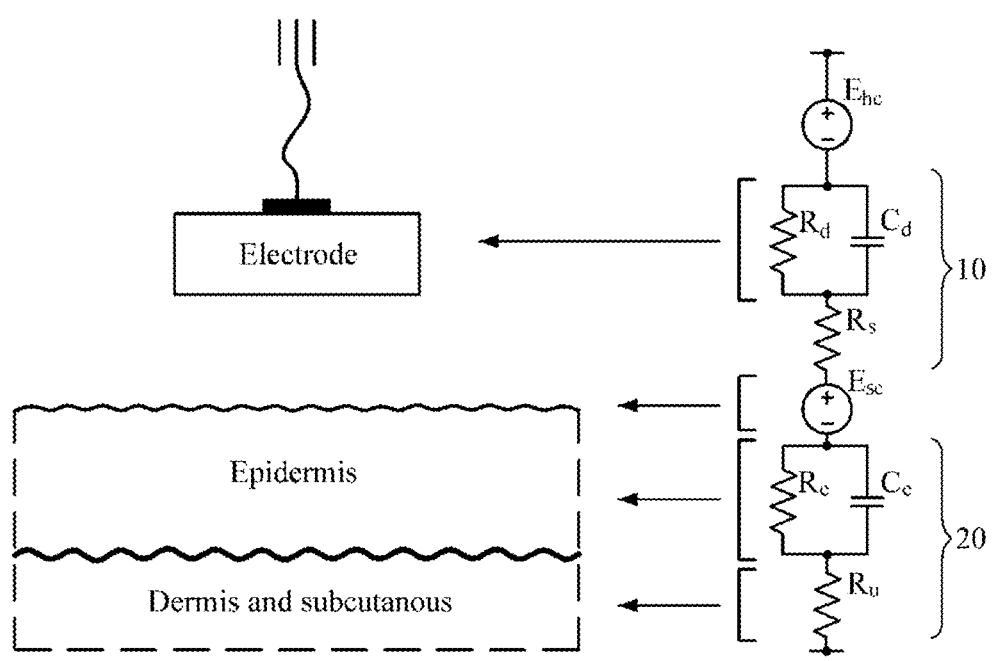
FIG. 1 is a diagram illustrating an example of an equivalent circuit when skin and an electrode come into contact with each other.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Hereinafter, embodiments of the disclosure will be described in detail with reference to the accompanying drawings. In the drawings, the same reference symbols refer to same parts although illustrated in other drawings. In the following description, a detailed description of known functions and configurations incorporated herein will be omitted when it may obscure the subject matter of the inventive concept.

Process steps described herein may be performed differently from a specified order, unless a specified order is clearly stated in the context of the disclosure. That is, each step may be performed in a specified order, at substantially the same time, or in a reverse order.

Further, the terms used throughout this specification are defined in consideration of the functions according to embodiments, and can be varied according to a purpose of a user or manager, or precedent and so on. Therefore, definitions of the terms may be made on the basis of the overall context.

It will be understood that, although the terms first, second, etc. may be used herein to describe various elements, these elements may not be limited by these terms. These terms are only used to distinguish one element from another. Any references to singular may include plural unless expressly stated otherwise. In the present specification, the terms, such as 'including' or 'having,' etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Further, components that will be described in the specification are discriminated according to functions mainly performed by the components. That is, two or more components that will be described later can be integrated into a single component. Furthermore, a single component that will be explained later can be separated into two or more components. Moreover, each component that will be described can additionally perform some or all of a function executed by another component in addition to the main function thereof. Some or all of the main function of each component that will be explained can be carried out by another component. Each component may be implemented as hardware, software, or a combination of both.

FIG. 1 is a diagram illustrating an example of an equivalent circuit when skin and an electrode come into contact with each other.

Referring to FIG. 1, when the electrode comes into contact with skin, the equivalent circuit may be represented as a contact impedance 10, which occurs by contact of the electrode with the skin, and a bio-impedance 20 that is indicative of an impedance in the skin.

The contact impedance 10 is a value that varies according to a physical contact area of the electrode and the skin. As the contact area of the electrode and the skin is increased, the contact impedance 10 is decreased, but the bio-impedance 20 is changed by a physiological change (e.g., perspiration, skin composition change, etc.), rather than by a physical contact of the electrode and the skin.

In the case in which an impedance is measured by contacting two electrodes and the skin of an object, the measured impedance of the object may be represented by a series connection of the contact impedance 10 and the bio-impedance 20. Here, a change in the physical contact area of the electrode and the object may affect the contact impedance 10, while having no effect on the bio-impedance 20, thereby leading to a change in the impedance of the object.

Accordingly, in one embodiment, by monitoring a change in the impedance of the object that is measured by contacting the electrode and the skin of the object, a contact state of the electrode with the skin of the object may be determined.

Figure 2:
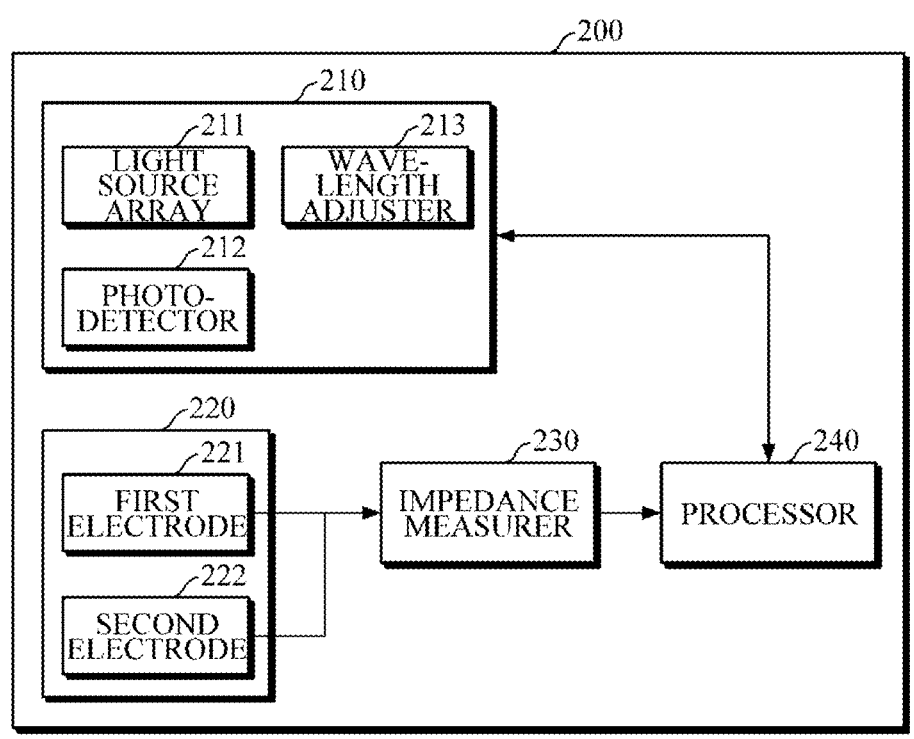
FIG. 2 is a block diagram illustrating an example of a bio-signal measuring apparatus.
Figure 3:
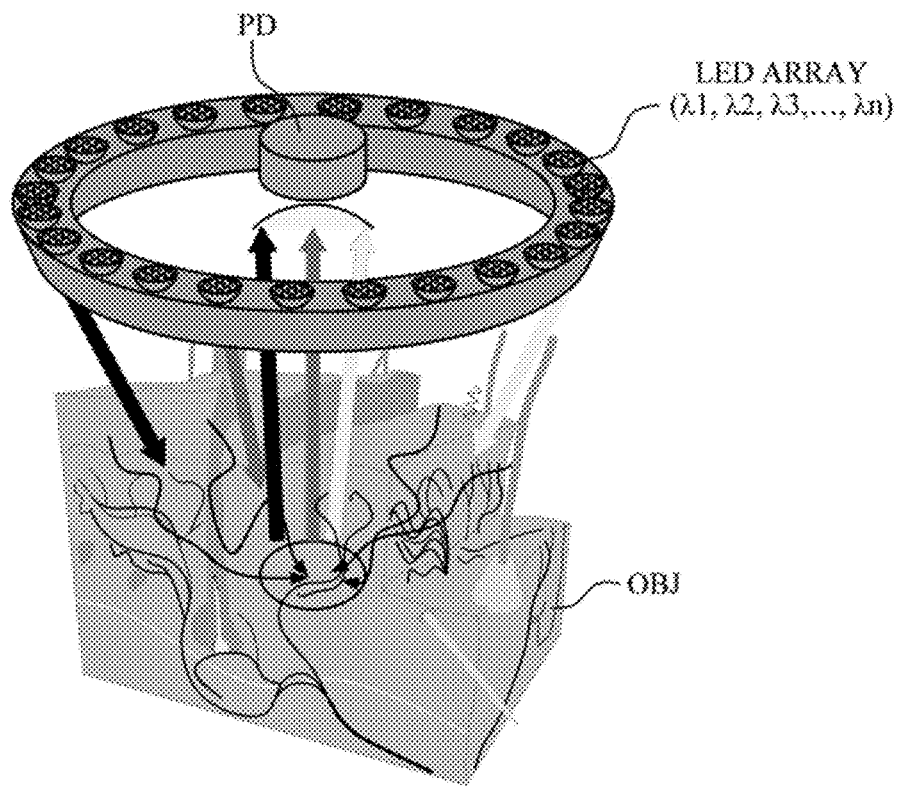
FIG. 3 is a diagram illustrating an example of an optical sensor.
Figure 4:
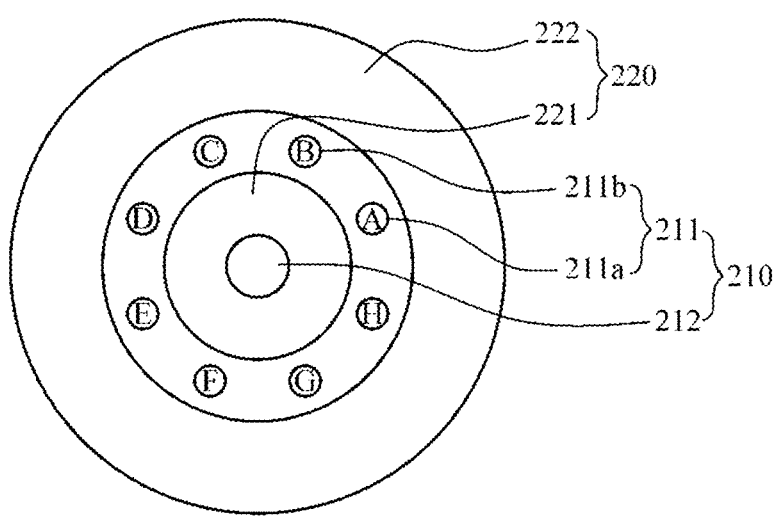
FIG. 4 is a diagram illustrating an example of an arrangement of an optical sensor and an electrode part.

FIG. 2 is a block diagram illustrating an example of a bio-signal measuring apparatus; FIG. 3 is a diagram illustrating an example of an arrangement of a light source array and a photodetector; and FIG. 4 is a diagram illustrating an example of an arrangement of an optical sensor and an electrode part.

A bio-signal measuring apparatus 200 of FIG. 2 may be embedded in an electronic device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a watch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto.

Referring to FIG. 2, the bio-signal measuring apparatus 200 includes an optical sensor 210, an electrode part 220, an impedance measurer 230, and a processor 240.

The optical sensor 210 may emit light onto an object, and may receive light reflected or scattered form the object. To this end, the optical sensor 210 may include a light source array 211, including a plurality of light sources, and a photodetector 212.

Each of the light sources of the light source array 211 may emit light of different wavelengths onto the object. For example, each of the light sources may emit light, e.g., Near Infrared Ray (NIR) onto the skin of the object. However, the wavelengths of light emitted from each of the light sources may vary depending on the purpose of measurement or the types of component to be measured. Further, each light source is not necessarily a single light source, but may be an array of a plurality of light sources. Each light source may include a light emitting diode (LED), a laser diode, a fluorescent body, and the like.

The photodetector 212 may receive an optical signal reflected or scattered from the object. The photodetector 212 may convert the received optical signal into an electric signal and may transmit the electric signal to the processor 240. In one embodiment, the photodetector 212 may include a photo diode, a photo transistor (PTr), a charge-coupled device (CCD), and the like. The photodetector 212 is not necessarily a single device, but may be an array of a plurality of devices.

A plurality of light sources of the light source array 211 may be arranged on an outer periphery of the photodetector 212 to surround or be around the photodetector 212. For example, the light source array 211 may be disposed in the form of a concentric circle centered on the photodetector 212 to surround or be around the photodetector 212.

For example, referring to FIG. 3, the optical sensor 210 may include a photodiode PD formed at the center thereof, and an LED array having n number of LEDs disposed on an outer periphery of the photodiode PD in the form of a concentric circle centered on the photodiode PD. The LEDs may be preset to have different peak wavelengths $\lambda_1, \lambda_2, \lambda_3,$ ..., and $\lambda_n$. For example, even if some of the light sources are set to have the same temperature, the light sources may have different peak wavelengths by shifting the peak wavelengths by minutely adjusting a current intensity, a pulse duration, and the like, of the light sources.

The optical sensor 210 may further include a wavelength adjuster 213 that adjusts a peak wavelength range of each light source of the light source array 211. FIG. 2 illustrates only one wavelength adjuster 213, but this is an example for convenience of explanation. That is, the wavelength adjuster 213 may be provided in number, corresponding to the total number of the light sources, to individually adjust peak wavelengths emitted by each light source onto an object OBJ. In this case, each wavelength adjuster 213 may be adhered to one surface of each light source, and may adjust a peak wavelength of each light source under the control of the processor 240.

For example, the wavelength adjuster 213 may be a temperature controlling member (e.g., resistance heating element, thermoelement, etc.), that adjusts a peak wavelength by controlling the temperature of each light source. However, the wavelength adjuster 213 is not limited thereto, and may be various members that may adjust a range of wavelengths emitted by light sources.

The electrode part 220 includes a first electrode 221 and a second electrode 222. The first electrode 221 may be disposed between the photodetector 212 and the light source array 211, and the second electrode 222 may be disposed on an outer periphery of the light source array 211. In one embodiment, the first electrode 221 and the second electrode 222 may be formed in a concentric ring shape based on the center of the optical sensor 210.

For example, referring to FIG. 4, the photodetector 212 is disposed at the center of the optical sensor 210, and a first electrode 221 having a concentric ring shape may be disposed on an outer periphery of the photodetector 212 to surround or be around the photodetector 212. Further, the light source array 211, formed in a concentric circle shape and having six light sources 211a and 211b disposed to surround or be around the first electrode 221, is disposed on an outer periphery of the first electrode 221; and the second electrode 222 having a concentric ring shape is disposed on an outer periphery of the light source array 211 to surround or be around the light source array 211. Although FIG. 4 illustrates an example of the six light sources 211a and 211b, the number of light sources is not limited thereto. That is, the number of light sources included in the optical sensor 210 may vary according to the types of object to be measured, an operating method of the optical sensor 210, and the like.

The first electrode 221 and the second electrode 222 may protrude from the surface of the bio-signal measuring apparatus 200, and a protruding height thereof may be equal to each other. Here, the protrusion from the surface of the bio-signal measuring apparatus 200 also includes a case in which a protruding height is 0, which indicates that the first electrode 221 and the second electrode 222 are embedded in the bio-signal measuring apparatus 200, such that the surface of the first electrode 221 and the second electrode 222 is parallel to the surface of the bio-signal measuring apparatus 200. However, a height of protrusion may vary according to the types of object to be measured by the first electrode 221 and the second electrode 222, an operating method or structure (e.g., a protruding height of the optical sensor 210, etc.) of the optical sensor 210, and the like. For example, a protruding height of the first electrode 221 and the second electrode 222 may be equal to a protruding height of the optical sensor 210, but is not limited thereto.

The impedance measurer 230 may measure an impedance of an object through the first electrode 221 and the second electrode 222. To this end, the impedance measurer 230 may include a power source, which applies a predetermined current to the object through the first electrode 221 and the second electrode 222, and a voltmeter that measures a voltage generated between the first electrode and the second electrode by the applied current. The impedance measurer 230 may obtain the impedance of the object by using a relational expression ($V=I*Z$) among the voltage, the current, and the impedance based on the applied current and the measured voltage.

However, there is no specific suggestion on the configuration of the impedance measurer 230 and a method of measuring the impedance. For example, the configuration and method of an impedance measurer, which is currently known in the art and is widely used, may also be used as well as the configuration and method of an impedance measurer to be used for future applications.

The processor 240 may control the overall operation of the bio-signal measuring apparatus 200.

The processor 240 may control the optical sensor 210 according to a user's request.

The processor 240 may control the light source array 211 to emit light onto an object. Before driving each light source of the light source array 211, the processor 240 may set a peak wavelength emitted from each light source. In this case, the processor 240 may control the wavelength adjuster 213 to set the peak wavelength of each light source.

Once the peak wavelength of each light source is set, the processor 240 may turn on the power of each light source, and may control each light source to emit light onto an object. In this case, the processor 240 may control turning on/off of each light source of the light source array 211 by time-dividing each light source. However, this is an example, and the processor 240 is not limited thereto, and may turn on the plurality of light sources all together so that the light sources may emit light at the same time. Further, the processor 240 may divide the light sources into two or more groups according to the preset peak wavelength, and may control each group of the divided light sources by time-dividing the light sources. However, this is an example, and a method of controlling the light sources may be adjusted based on various types of information such as a battery state, an application area of the optical sensor 210, the size of the photodetector 212, and the like.

In this case, driving conditions, such as an emission time, a driving order, a current intensity, a pulse duration, and the like, may be preset for each light source, and the processor 240 may control a method of driving each light source by reference to the preset light source driving conditions. In addition, by driving each light source according to the current intensity and pulse duration of a light source to be driven, the processor 240 may shift the peak wavelength of a light source, which is set by controlling temperature, to other wavelength. In this manner, the processor 240 may set the peak wavelength of the plurality of light sources at narrower wavelength spacing.

The processor 240 may control the impedance measurer 230. For example, the processor 240 may control the impedance measurer 230 to measure the impedance of an object.

The processor 240 may determine a contact state of the optical sensor 210 with the object based on the impedance of the object that is measured by the impedance measurer 230. In one embodiment, the processor 240 may compare the measured impedance of the object with a predetermined threshold value, and may determine the contact state of the optical sensor 210 with the object based on the comparison. For example, in the case in which the measured impedance of the object is equal to or lower than the predetermined threshold value, the processor 240 may determine that the contact state between the object and the optical sensor 210 is good; and in the case in which the measured impedance of the object exceeds the predetermined threshold value, the processor 240 may determine that the contact state between the object and the optical sensor 210 is poor. In this case, the good contact state indicates a state in which the object and the optical sensor 210 contact each other fully enough to allow the optical sensor 210 to measure a valid optical signal; and a poor contact state indicates a state in which the object and the optical sensor 210 incompletely contact each other, or some or all of the portions of the object and the optical sensor 210 are separated from each other, such that the optical sensor 210 may not measure a valid optical signal.

In the case in which the object fully contacts each of the electrodes 221 and 222, a contact area of the object and the electrodes 221 and 222 is maximized, such that the impedance (more specifically contact impedance) of the object is minimized. By contrast, in the case in which the object incompletely contacts each of the electrodes 221 and 222, or some or all of the portions of the object and each of the electrodes 221 and 222 are separated from each other, the contact area of the object and each of the electrodes 221 and 222 is reduced, such that the impedance (more specifically contact impedance) of the object is increased. That is, the impedance (more specifically contact impedance) of the object varies according to the contact state of the object and the electrode part 220. The contact state of the object and the electrode part 220 may not be completely the same as the contact state of the object and the optical sensor 210, because the two contact states are different in terms of subject. However, the optical sensor 210 is disposed on the inner side of the second electrode 222, such that in the case in which the object and the electrode part 220 fully contact each other, and the impedance of the object is equal to or lower than a predetermined threshold value, the contact state between the object and the optical sensor 210 may be considered to be good, and in the case in which the object and the electrode part 220 incompletely contact each other, or some or all of the portions of the object and the electrode part 220 are separated from each other and the impedance of the object exceeds a predetermined threshold value, the contact state between the object and the optical sensor 210 may be considered to be poor.

The processor 240 may perform a predetermined function in response to a determination result of the contact state of the object and the optical sensor 210.

In one embodiment, upon determining that the contact state between the object and the optical sensor 210 is good, the processor 240 may estimate bio-information of the object based on the optical signal received from the photodetector 212. For example, the processor 240 may reconstruct a spectrum of the object based on the optical signal received from the photodetector 212, and may estimate bio-information of the object by analyzing the reconstructed spectrum of the object. In this case, the bio-information may include blood pressure, vascular age, degree of arteriosclerosis, cardiac output, vascular compliance, blood glucose, triglyceride, cholesterol, protein, uric acid, peripheral vascular resistance, and the like.

In another example, upon determining that the contact state between the object and the optical sensor 210 is poor, the processor 240 may perform functions, such as generating an alarm and/or guide information, stopping measuring an optical signal by the optical sensor 210, ignoring an optical signal measured by the optical sensor 210, and/or correcting an optical signal measured by the optical sensor 210. For example, upon determining that the contact state between the object and the optical sensor 210 is poor, the processor 240 may generate a predetermined alarm and/or guide information, and may output the generated alarm and/or guide information through an output interface. In this case, the guide information may include information for inducing complete contact of the object with the optical sensor 210 to improve a contact state between the object and the optical sensor 210. In another example, upon determining that the contact state between the object and the optical sensor 210 is poor, the processor 240 may halt the operation of the optical sensor 210 and may stop measuring the optical signal by the optical sensor 210 until the processor 240 determines that the contact state between the object and the optical sensor 210 is good. In yet another example, upon determining that the contact state between the object and the optical sensor 210 is poor, the processor 240 may continue to measure the optical signal by the optical sensor 210, but may ignore an optical signal measured when the contact state is poor, and may not reflect the optical signal in analysis data. In still another example, upon determining that the contact state between the object and the optical sensor 210 is poor, the processor 240 may correct a measured optical signal by using a correction model that defines a relationship between impedance and an optical signal. In this case, the correction model may be pre-generated and stored in an internal or external database.

Figure 5:
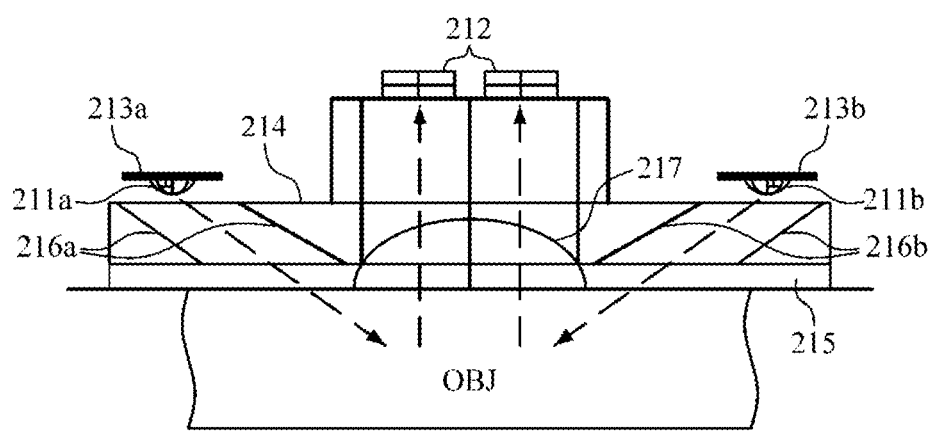
FIG. 5 is a diagram schematically illustrating a structure of an optical sensor.

FIG. 5 is a diagram schematically illustrating a structure of an optical sensor.

The structure of the optical sensor 210 will be described in further detail by reference to FIGS. 2 and 5.

By referring to FIGS. 2 and 5, the optical sensor 210 includes a housing 214 in which each of the light sources 211a and 211b, the photodetector 212, and the like may be mounted. FIG. 5 illustrates the light sources 211a and 211b and the photodetector 212 are two in number respectively, which is an example, and the number thereof is not specifically limited.

Further, the optical sensor 210 may include a cover 215 formed at the bottom thereof where the optical sensor 210 contacts an object OBJ. In this case, the cover 215 may be made of anti-reflection coated glass.

In addition, the optical sensor 210 may further include direction adjusters 216a and 216b that are mounted in the housing 214 and adjust the direction of light emitted by the light sources 211a and 211b. The direction adjusters 216a and 216b adjust the direction of light, emitted by the light sources 211a and 211b, to be directed toward a portion to be examined of the object OBJ, and may be an optical mirror. The direction and angle of the direction adjuster 216a and 216b may be preset at the initial operation, but is not limited thereto, and may be automatically adjusted under the control of the processor 240.

Light, emitted by the light sources 211a and 211b, enters into the object OBJ along a light path as indicated by an arrow, and is reflected or scattered from the object OBJ depending on tissue properties of the object OBJ to travel toward the photodetector 212. The photodetector 212 detects light returning from the object OBJ. In this case, the optical sensor 210 may include a light concentrator 217 that concentrates light, reflected or scattered from the object, to be directed toward the photodetector 212. In this case, the light concentrator 217 may be an optical module such as an optical lens.

Further, wavelength adjusters 213a and 213b may be adhered to one surface of the light sources 211a and 211b. In this case, the wavelength adjusters 213a and 213b may be detachable from the respective light sources 211a and 211b, or may be integrally formed therewith; and may be a temperature controlling member, such as a resistance heating element or a thermoelement, which controls temperature of the light sources 211a and 211b.

The processor 240 may be electrically connected with the wavelength adjusters 213a and 213b and the light sources 211a and 211b, and may control each of the wavelength adjusters 213a and 213b so that the light sources 211a and 211b to be driven may emit light of a predetermined peak wavelength range.

In one embodiment, the first electrode 221 may be formed in a concentric ring shape, so that the first electrode 221, which is disposed between the photodetector 212 and the light sources 211a and 211b, may surround or be around the photodetector 212; and the second electrode 222 may be formed in a concentric ring shape, so that the second electrode 222, which is disposed on an outer periphery of the light source array including the light sources 211a and 211b, may surround or be around the light sources 211a and 211b.

That is, referring to FIGS. 4 and 5, the first electrode 221 may be disposed on an outer periphery of the photodetector 212 to surround or be around the photodetector 212, and the second electrode 222 may be disposed on an outer periphery of the light source array 211 to surround or be around the light source array 211. Thus, the first electrode 221 is disposed in a region of the cover 215 between the light source array 211 and the photodetector 212, and the second electrode 222 is disposed in a region of the cover 215 of an outer side the light source array 211.

Figure 6A:
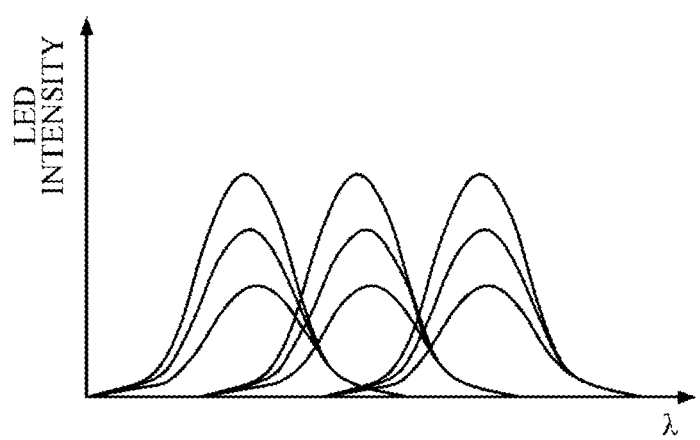
FIGS. 6A, 6B and 6C are diagrams explaining an example of reconstructing a spectrum by a processor.
Figure 6B:
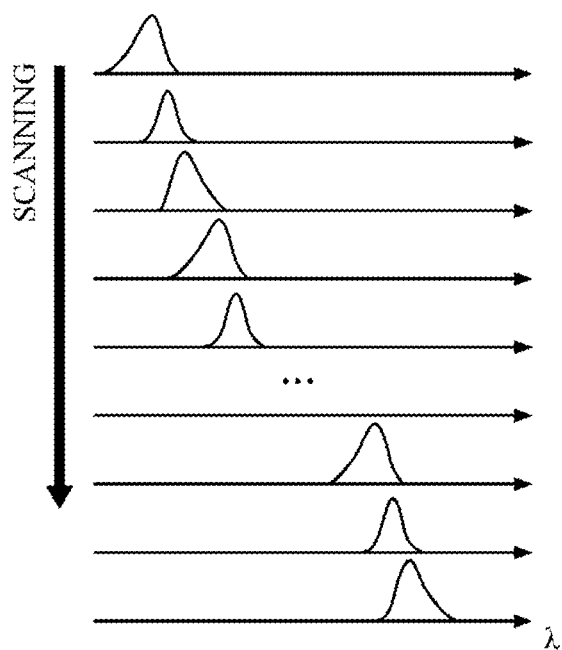
Figure 6C:
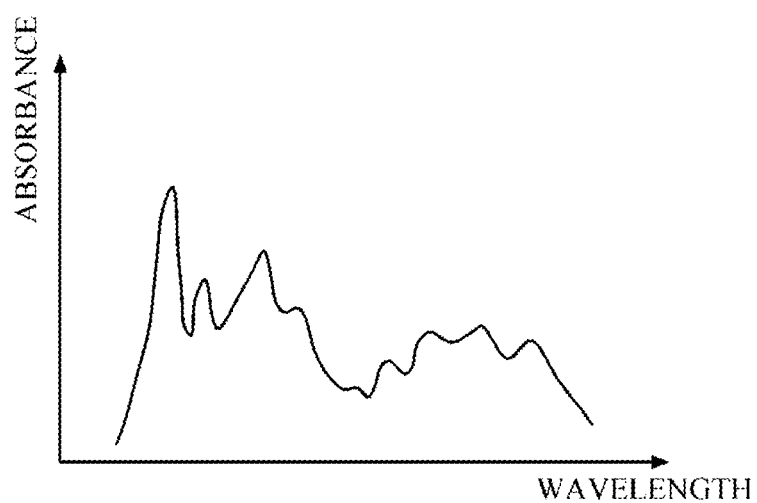

FIGS. 6A, 6B and 6C are diagrams explaining an example of reconstructing a spectrum by a processor.

Referring to FIGS. 3 and 6A, a light source array is an LED array having n number of LEDs. The LEDs may be preset to have different peak wavelengths $\lambda_1, \lambda_2, \lambda_3, \ldots,$ and $\lambda_n$ based on light source driving conditions (e.g., temperature, current intensity, pulse duration, etc.). For example, even if some of the light sources are set to have the same temperature, the light sources may have different peak wavelengths by shifting the peak wavelengths by minutely adjusting a current intensity, a pulse duration, and the like, of the light sources.

Referring to FIG. 6B, the processor may sequentially drive the light sources based on a set driving order, a pulse duration, and the like to emit light, and the photodetector PD detects light returning from the object OBJ. In this case, the processor may drive only some of the light sources, and may divide the light sources into groups so that the processor may drive the light sources by time-dividing the light sources by each group.

Referring to FIG. 6C, the processor may receive an optical signal detected by the photodetector PD, and may reconstruct a spectrum. In this case, the processor may reconstruct the spectrum by using the Tikhonov regularization method for solving an ill-posed problem by using the following Equations 1 and 2.

$$Az = U \quad \text{[Equation 1]}$$

Herein, A is a matrix of reference spectrum properties measured according to driving conditions of each light source; U is a matrix of values actually measured by the photodetector according to driving conditions equally set for each light source; and z is a reconstructed spectrum.

$$(\alpha E + A^T A) Z_\alpha = A^T u$$

$$Z_\alpha = (\alpha E + A^T A)^{-1} A^T u \quad \text{[Equation 2]}$$

Herein, u is each component of a matrix U actually measured by the photodetector; E is a unit matrix; A is a kernel matrix, and a matrix of a reference spectrum measured for each light source according to driving conditions of the light sources; $\alpha$ is a unit of noise removal; T is a transpose of a matrix; and Z is a reconstructed spectrum.

Figure 7:
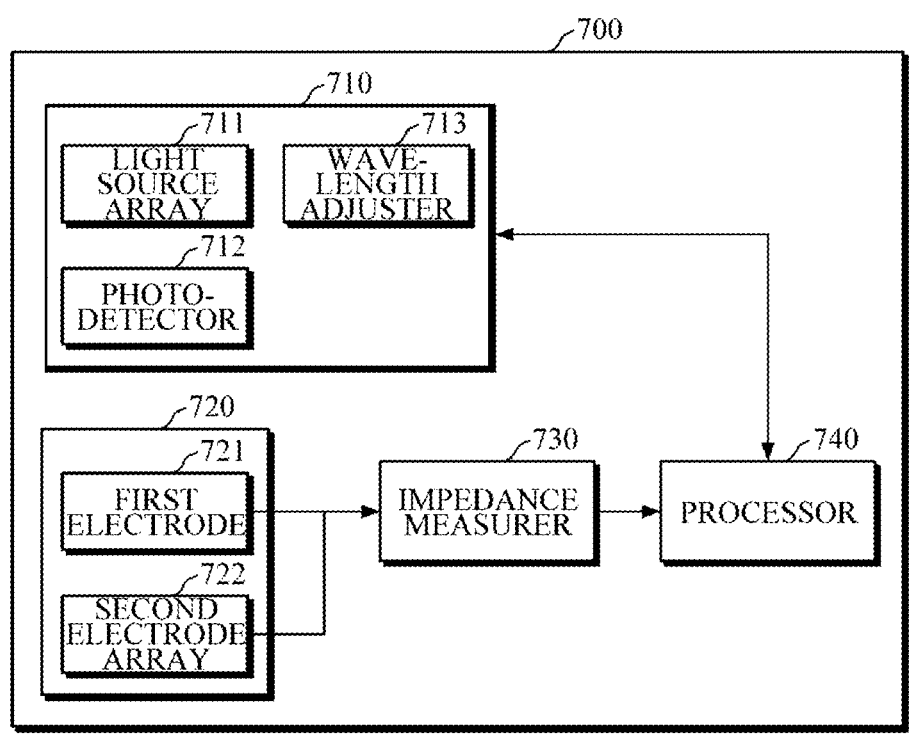
FIG. 7 is a block diagram illustrating another example of a bio-signal measuring apparatus.
Figure 8:
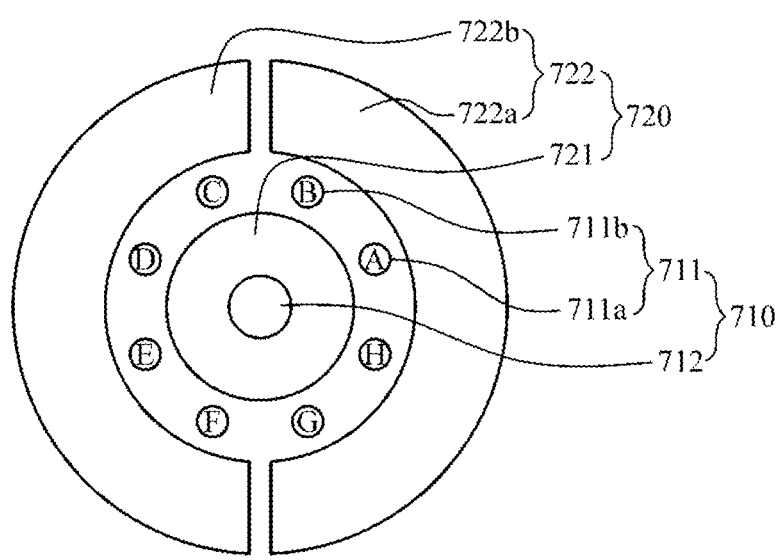
FIG. 8 is a diagram illustrating an example of an arrangement of an optical sensor and an electrode part.
Figure 9:
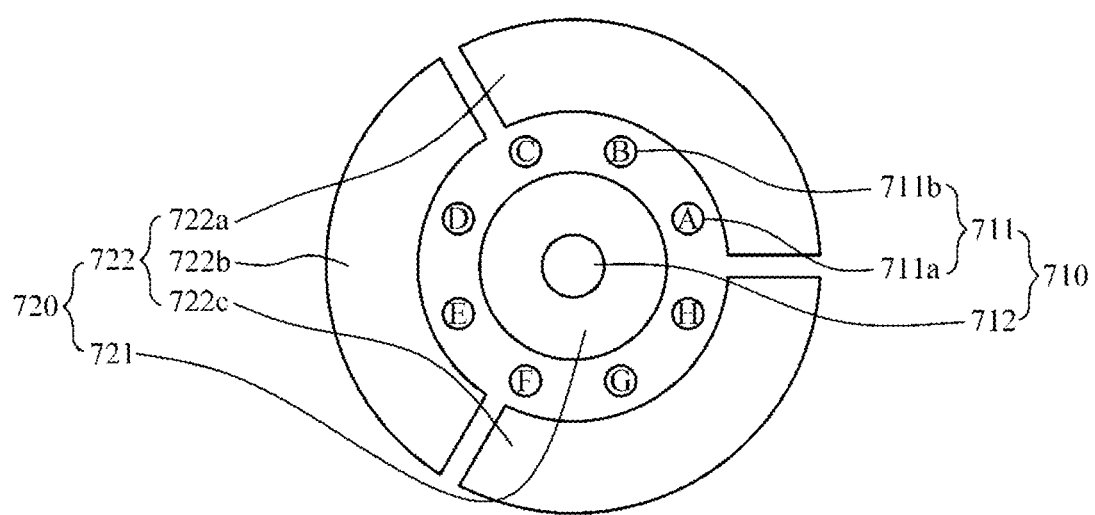
FIG. 9 is a diagram illustrating another example of an arrangement of an optical sensor and an electrode part.
Figure 10:
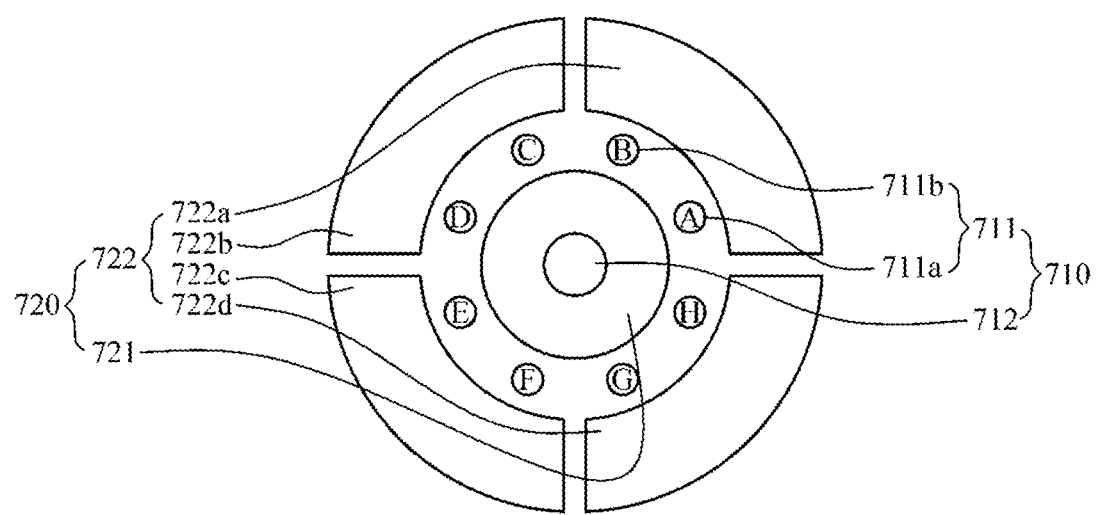
FIG. 10 is a diagram illustrating yet another example of an arrangement of an optical sensor and an electrode part.

FIG. 7 is a block diagram illustrating another example of a bio-signal measuring apparatus; FIG. 8 is a diagram illustrating an example of an arrangement of an optical sensor and an electrode part; FIG. 9 is a diagram illustrating another example of an arrangement of an optical sensor and an electrode part; and FIG. 10 is a diagram illustrating yet another example of an arrangement of an optical sensor and an electrode part.

A bio-signal measuring apparatus 700 of FIG. 7 may be embedded in an electronic device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a watch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto.

Referring to FIGS. 7 to 10, the bio-signal measuring apparatus 700 includes an optical sensor 710, an electrode part 720, an impedance measurer 730, and a processor 740.

The optical sensor 710 may emit light onto an object, and may receive light reflected or scattered form the object. To this end, the optical sensor 710 may include a light source array 711 including a plurality of light sources and a photodetector 712.

Each of the light sources of the light source array 711 may emit light of different wavelengths onto the object. For example, each of the light sources may emit light, e.g., Near Infrared Ray (NIR) onto the skin of the object. However, the wavelengths of light emitted from each of the light sources may vary depending on the purpose of measurement or the types of component to be measured. Further, each light source is not necessarily a single light source, but may be an array of a plurality of light sources. Each light source may include a light emitting diode (LED), a laser diode, a fluorescent body, and the like.

The photodetector 712 may receive an optical signal reflected or scattered from the object. The photodetector 712 may convert the received optical signal into an electric signal and may transmit the electric signal to the processor 740. In one embodiment, the photodetector 712 may include a photo diode, a photo transistor (PTr), a charge-coupled device (CCD), and the like. The photodetector 712 is not necessarily a single device, but may be an array of a plurality of devices.

The light source array 711 may be arranged to surround or be around the photodetector 712. For example, the plurality of light sources of the light source array 711 may be disposed in the form of a concentric circle centered on the photodetector 712 to surround or be around the photodetector 712.

In addition, the optical sensor 710 may further include a wavelength adjuster 713 that adjusts a peak wavelength range of each light source of the light source array 711.

The electrode part 720 includes a first electrode 721, which contacts an object, and a second electrode array 722 having a plurality of second electrodes. The first electrode 721 may be disposed between the photodetector 712 and the light source array 711, and the second electrode array 722 may be disposed on an outer periphery of the light source array 711 to surround or be around the light source array 711. In one embodiment, the first electrode 721 and the second electrode array 722 may be formed in a concentric ring shape based on the center of the optical sensor 710.

For example, referring to FIG. 8, one photodetector 712 may be disposed at the center of the optical sensor 710, and a first electrode 721 having a concentric ring shape may be disposed on an outer periphery of the photodetector 712 to surround or be around the photodetector 712. Further, the light source array 711, formed in a concentric circle shape and having six light sources 711a and 711b disposed to surround or be around the first electrode 721, is disposed on an outer periphery of the first electrode 721; and the second electrode array 722, formed in a concentric ring shape and having two second electrodes 722a and 722b disposed to surround or be around the light source array 711, is disposed on an outer periphery of the light source array 711. Although FIG. 8 illustrates an example of the six light sources 711a and 711b, the number of light sources is not limited thereto. That is, the number of light sources included in the optical sensor 710 may vary according to the types of object to be measured, an operating method of the optical sensor 710, and the like. Further, the size and/or surface area of the two second electrodes 722a and 722b may be equal to or different from each other.

In another example, referring to FIG. 9, one photodetector 712 is disposed at the center of the optical sensor 710, and a first electrode 721 having a concentric ring shape is disposed on an outer periphery of the photodetector 712 to surround or be around the photodetector 712. Further, the light source array 711, formed in a concentric circle shape and having the six light sources 711a and 711b disposed to surround or be around the first electrode 721, is disposed on an outer periphery of the first electrode 721; and the second electrode array 722, formed in a concentric ring shape and having three second electrodes 722a, 722b, and 722c disposed to surround or be around the light source array 711, is disposed on an outer periphery of the light source array 711. Although FIG. 9 illustrates an example of the six light sources 711a and 711b, the number of light sources is not limited thereto. That is, the number of light sources included in the optical sensor 710 may vary according to the types of object to be measured, an operating method of the optical sensor 710, and the like. Further, the size and/or surface area of the three second electrodes 722a, 722b, and 722c may be equal to or different from each other.

In yet another example, referring to FIG. 10, one photodetector 712 is disposed at the center of the optical sensor 710, and a first electrode 721 having a concentric ring shape is disposed on an outer periphery of the photodetector 712 to surround or be around the photodetector 712. Further, the light source array 711, formed in a concentric circle shape and having six light sources 711a and 711b disposed to surround or be around the first electrode 721, is disposed on an outer periphery of the first electrode 721; and the second electrode array 722, formed in a concentric ring shape and having four second electrodes 722a, 722b, 722c, and 722d disposed to surround or be around the light source array 711, is disposed on an outer periphery of the light source array 711. Although FIG. 10 illustrates an example of six light sources 711a and 711b, the number of light sources is not limited thereto. That is, the number of light sources included in the optical sensor 710 may vary according to the types of object to be measured, an operating method of the optical sensor 710, and the like. Further, the size and/or surface area of the four second electrodes 722a, 722b, 722c, and 722d may be equal to or different from each other.

FIGS. 8 to 10 illustrate an example of two to four second electrodes, but the number of the second electrodes is not limited thereto. That is, the number of the second electrodes may vary according to the performance and usage of a system, the number of light sources, and the like.

The first electrode 721 and each second electrode of the second electrode array 722 may protrude from the surface of the bio-signal measuring apparatus 700, and the protruding height thereof may be equal to each other. Here, the protrusion from the surface of the bio-signal measuring apparatus 700 also includes a case in which a protruding height is 0, which indicates that the first electrode 721 and each second electrode of the second electrode array 722 are embedded in the bio-signal measuring apparatus 700, such that the surface of the first electrode 721 and each second electrode of the second electrode array 722 is parallel to the surface of the bio-signal measuring apparatus 700. However, a height of protrusion may vary according to the types of object to be measured by the first electrode 721 and the second electrode array 722, an operating method or structure (e.g., a protruding height of the optical sensor 710, etc.) of the optical sensor 710, and the like. For example, a protruding height of the first electrode 721 and the second electrode array 722 may be equal to a protruding height of the optical sensor 710, but is not limited thereto.

The impedance measurer 730 may measure an impedance of the object for each electrode through the first electrode 721 and each second electrode of the second electrode array 722. To this end, the impedance measurer 730 may include a power source that applies a predetermined current to the object through the first electrode 721 and each second electrode of the second electrode array 722, a voltmeter that measures a voltage generated between the first electrode 721 and each second electrode of the second electrode array 722 by the applied current, and the like. The impedance measurer 730 may obtain the impedance of the object for each electrode based on the applied current and the measured voltage by using the relational expression (V=I*Z) among a voltage, a current, and an impedance. For example, as illustrated in FIG. 8, in the case in which the second electrode array 722 includes two second electrodes 722a and 722b, the impedance measurer 730 may apply a current to the object through the first electrode 721 and the second electrode 722a, and may measure an impedance (first impedance) by measuring a voltage generated between the first electrode 721 and the second electrode 722a; and may apply a current to the object through the first electrode 721 and the second electrode 722b, and may measure an impedance (second impedance) by measuring a voltage generated between the first electrode 721 and the second electrode 722b.

The processor 740 may control the overall operation of the bio-signal measuring apparatus 700.

The processor 740 may control the optical sensor 710 according to a user's request. In this case, the processor 740 may control turning on/off of each light source of the light source array 711 by time-dividing each light source. The processor 740 may drive each light source based on driving conditions such as a current intensity, a pulse duration, and the like. However, the processor 740 is not limited thereto, and may turn on the plurality of light sources all together so that the light sources may emit light at the same time.

The processor 740 may control the impedance measurer 730. For example, the processor 740 may control the impedance measurer 730 to measure the impedance of an object for each electrode.

The processor 740 may determine a contact state between the object and the optical sensor 710 based on the impedance of the object for each electrode, which is measured by the impedance measurer 730, and in case of a contact failure between the object and the optical sensor 710, the processor 740 may determine a location of the contact failure. In one embodiment, the processor 740 may compare each impedance of the object for each electrode with a predetermined threshold value, and may determine a contact state between the object and the optical sensor 210 based on the comparison; and in case of a contact failure between the object and the optical sensor 710, the processor 740 may determine a location of the contact failure. For example, in the case in which all the impedances of the object for each electrode is equal to or lower than the predetermined threshold value, the processor 740 may determine that the contact state between the object and the optical sensor 710 is good, and in the case in which one or more impedances for each electrode exceed the predetermined threshold value, the processor 740 may determine that the contact state between the object and the optical sensor 710 is poor. In this case, the processor 740 may determine that the contact failure occurs in a direction of the second electrode where the impedance, which exceeds the predetermined threshold value, is measured. For example, as illustrated in FIG. 7, in the case in which the impedance measurer 730 measures the first impedance of the object through the first electrode 721 and the second electrode 722a, and measures the second impedance of the object through the first electrode 721 and the second electrode 722b, it is assumed that the first impedance is equal to or lower than a predetermined threshold value, while the second impedance exceeds the predetermined threshold value. In this case, the processor 740 may determine a poor contact state in a direction of the second electrode 722b where the second impedance is measured.

The processor 740 may perform a predetermined function in response to the determination of the contact state between the object and the optical sensor 710.

In one embodiment, upon determining that the contact state between the object and the optical sensor 710 is good, the processor 740 may estimate bio-information of the object based on the optical signal received from the photodetector 712. For example, the processor 740 may reconstruct a spectrum of the object based on the optical signal received from the photodetector 712, and may estimate bio-information of the object by analyzing the reconstructed spectrum of the object. In this case, the bio-information may include blood pressure, vascular age, degree of arteriosclerosis, cardiac output, vascular compliance, blood glucose, triglyceride, cholesterol, protein, uric acid, peripheral vascular resistance, and the like. The method of reconstructing the spectrum is described above with reference to FIGS. 6A to 6C, such that detailed description thereof will be omitted.

In another example, upon determining that the contact state between the object and the optical sensor 710 is poor, the processor 740 may perform functions, such as generating an alarm and/or guide information, stopping measuring an optical signal by the optical sensor 710, ignoring an optical signal measured by the optical sensor 710, and/or correcting an optical signal measured by the optical sensor 710. For example, upon determining that the contact state of the object and the optical sensor 710 is poor, the processor 740 may generate a predetermined alarm and/or guide information, and may output the generated alarm and/or guide information through an output interface. In this case, the guide information may include information for inducing complete contact of the object with the optical sensor 710 to improve a contact state between the object and the optical sensor 710. In another example, upon determining that the contact state between the object and the optical sensor 710 is poor, the processor 740 may halt the operation of the optical sensor 710 and may stop measuring the optical signal by the optical sensor 710 until the processor 740 determines that the contact state between the object and the optical sensor 710 is good. In yet another example, upon determining that the contact state between the object and the optical sensor 710 is poor, the processor 740 may continue to measure the optical signal by the optical sensor 710, but may ignore an optical signal measured after being emitted from a light source in a location of the contact failure, and may not reflect the optical signal in analysis data. In still another example, upon determining that the contact state between the object and the optical sensor 710 is poor, the processor 740 may correct an optical signal measured after being emitted from a light source in a location of the contact failure based on the impedance for each electrode in the location of the contact failure. In this case, the processor 740 may use a correction model that defines a relationship between impedance and an optical signal. The correction model may be pre-generated and stored in an internal or external database.

Figure 11:
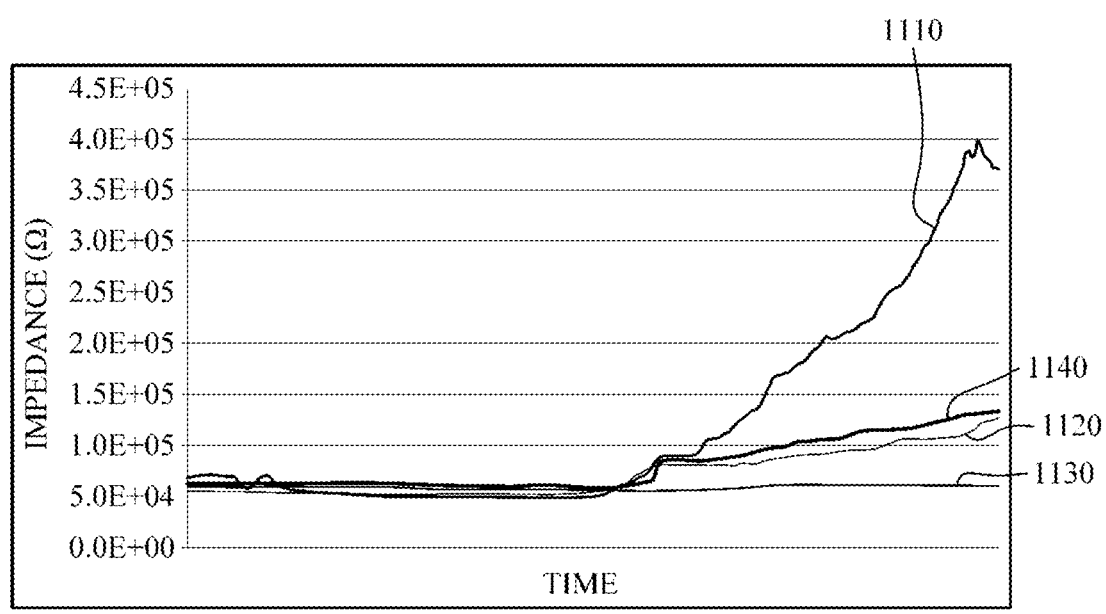
FIG. 11 is a diagram illustrating an example of an impedance for each electrode.
Figure 12:
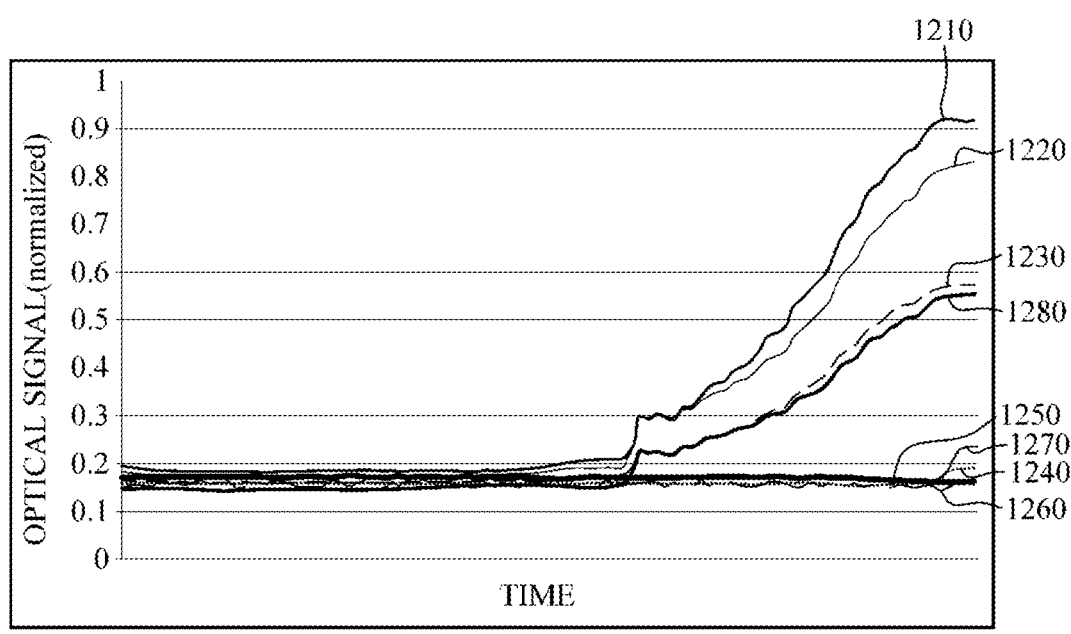
FIG. 12 is a diagram illustrating an example of an optical signal measured after being emitted from each light source.

FIG. 11 is a diagram illustrating an example of an impedance for each electrode, and FIG. 12 is a diagram illustrating an example of an optical signal measured after being emitted from each light source. FIGS. 11 and 12 are examples of measurement by a bio-signal measuring apparatus having the optical sensor and the electrode part of FIG. 10.

In FIG. 11, a reference numeral 1110 denotes an impedance measured through the first electrode 721 and the second electrode 722*a*; a reference numeral 1120 denotes an impedance measured through the first electrode 721 and the second electrode 722*b*; a reference numeral 1130 denotes an impedance measured through the first electrode 721 and the second electrode 722*c*; and a reference numeral 1140 denotes an impedance measured through the first electrode 721 and the second electrode 722*d*. Further, in FIG. 12, a reference numeral 1210 denotes an optical signal measured after being emitted from a light source A; a reference numeral 1220 denotes an optical signal measured after being emitted from a light source B; a reference numeral 1230 denotes an optical signal measured after being emitted from a light source C; a reference numeral 1240 denotes an optical signal measured after being emitted from a light source D; a reference numeral 1250 denotes an optical signal measured after being emitted from a light source E; a reference numeral 1260 denotes an optical signal measured after being emitted from a light source F; a reference numeral 1270 denotes an optical signal measured after being emitted from a light source G; and a reference numeral 1280 denotes an optical signal measured after being emitted from a light source H.

Referring to FIGS. 10 to 12, it can be seen that the impedance 1110 measured through the first electrode 721 and the second electrode 722*a*, the impedance 1120 measured through the first electrode 721 and the second electrode 722*b*, and the impedance 1140 measured through the first electrode 721 and the second electrode 722*d* are increased, and at the same time, the optical signal 1210 measured after being emitted from the light source A, the optical signal 1220 measured after being emitted from the light source B, the optical signal 1230 measured after being emitted from the light source C, and the optical signal 1280 measured after being emitted from the light source H are increased. That is, it can be seen that the contact failure has occurred in a direction of the second electrode 722*a*, and has caused the impedances 1110, 1120, and 1140 to be increased, and the optical signals 1210, 1220, 1230, and 1280 to be increased. Further, it can also be seen that there is a correlation between the increase of the impedances 1110, 1120, and 1140 and the increase of the optical signals 1210, 1220, 1230, and 1280.

Accordingly, a correction model may be generated based on such correlation, and the bio-signal measuring apparatus 700 may correct an optical signal, which is measured based on the impedance for each electrode in a location of the contact failure, by using the pre-generated correction model.

Figure 13:
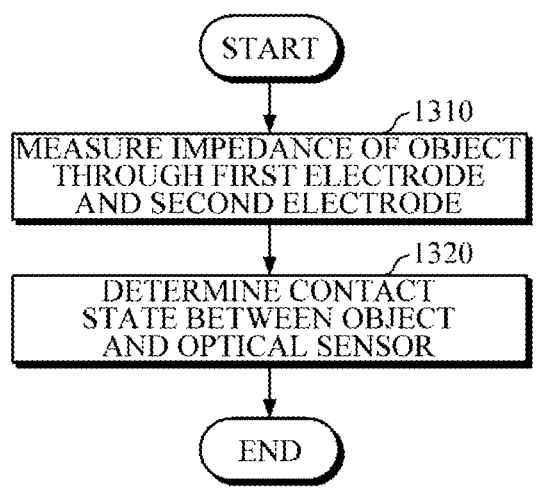
FIG. 13 is a flowchart illustrating an example of a method of determining a contact state.

FIG. 13 is a flowchart illustrating an example of a method of determining a contact state. The method of determining a contact state of FIG. 13 may be performed by the bio-signal measuring apparatus 200 of FIG. 2.

Referring to FIGS. 2 and 13, the bio-signal measuring apparatus 200 may measure an impedance of an object through the first electrode 221 and the second electrode 222 in operation 1310. In this case, an arrangement of the first electrode 221 and the second electrode 222 is described above with reference to FIGS. 2 to 4, such that detailed description thereof will be omitted. In one embodiment, the bio-signal measuring apparatus 200 may apply a predetermined current to the object through the first electrode 221 and the second electrode 222, may measure a voltage generated between the first electrode 221 and the second electrode 222 by the applied current, and may obtain an impedance of the object by using the relational expression (V=I*Z) among the voltage, the current, and the impedance based on the applied current and the measured voltage.

The bio-signal measuring apparatus 200 may determine a contact state between the object and the optical sensor 210 based on the impedance of the object in operation 1320. In one embodiment, in response to the impedance of the object being equal to or lower than a predetermined threshold value, the bio-signal measuring apparatus 200 may determine that the contact state between the object and the optical sensor 210 is good; and in response to the impedance of the object exceeding the predetermined threshold value, the bio-signal measuring apparatus 200 may determine that the contact state between the object and the optical sensor 210 is poor. In this case, the good contact state indicates a state in which the object and the optical sensor 210 contact each other fully enough to allow the optical sensor 210 to measure a valid optical signal; and a poor contact state indicates a state in which the object and the optical sensor 210 incompletely contact each other, or some or all of the portions of the object and the optical sensor 210 are separated from each other, such that the optical sensor 210 may not measure a valid optical signal.

Figure 14:
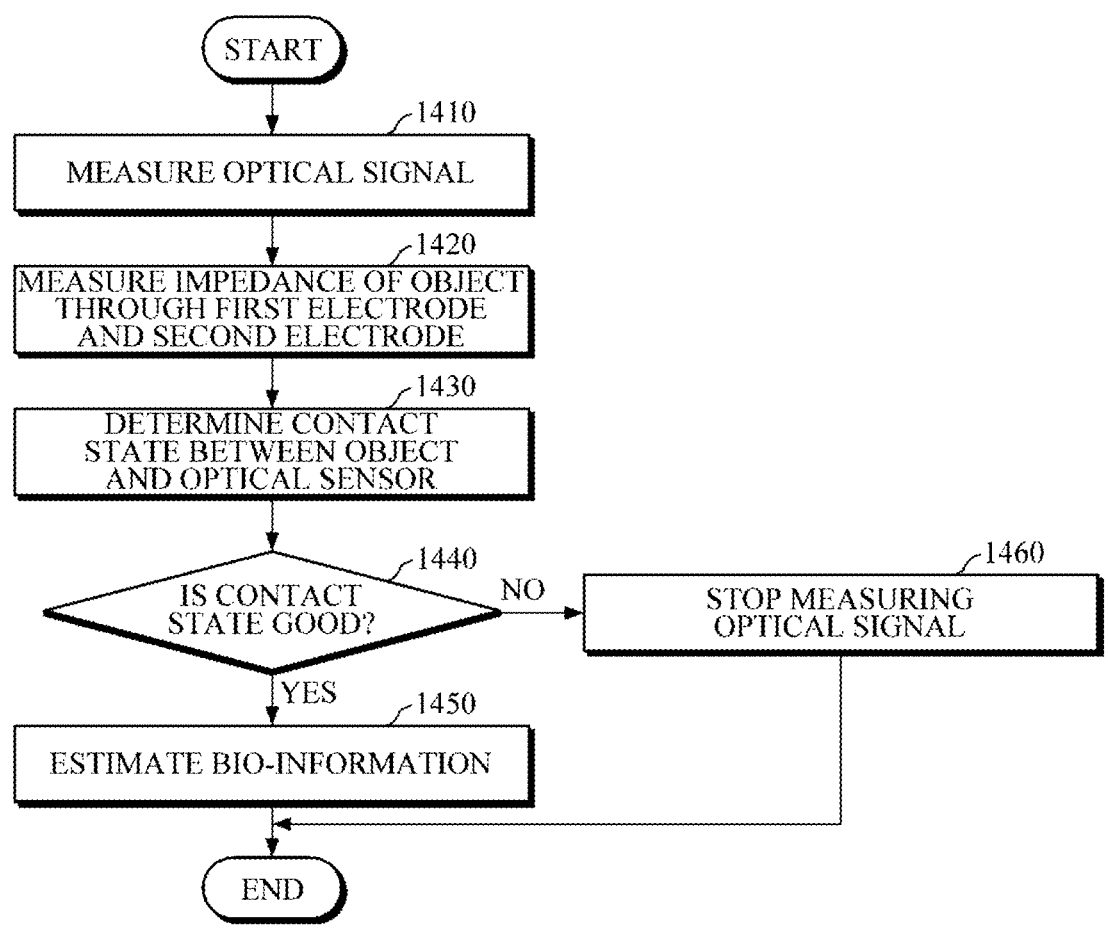
FIG. 14 is a flowchart illustrating an example of a bio-signal measuring method.

FIG. 14 is a flowchart illustrating an example of a bio-signal measuring method. The bio-signal measuring method of FIG. 14 may be performed by the bio-signal measuring apparatus 200 of FIG. 2.

Referring to FIGS. 2 and 14, the bio-signal measuring apparatus 200 may emit light onto an object by using the optical sensor 210, and may measure an optical signal of the object by receiving light reflected or scattered form the object in operation 1410.

The bio-signal measuring apparatus 200 may measure an impedance of the object through the first electrode 221 and the second electrode 222 in operation 1420. In this case, an arrangement of the first electrode 221 and the second electrode 222 is described above with reference to FIGS. 2 to 4, such that detailed description thereof will be omitted.

The bio-signal measuring apparatus 200 may determine a contact state between the object and the optical sensor 210 based on the impedance of the object in operation 1430. For example, in response to the impedance of the object being equal to or lower than a predetermined threshold value, the bio-signal measuring apparatus 200 may determine that the contact state between the object and the optical sensor 210 is good; and in response to the impedance of the object exceeding the predetermined threshold value, the bio-signal measuring apparatus 200 may determine that the contact state between the object and the optical sensor 210 is poor.

Upon determining that the contact state is good in operation 1440, the bio-signal measuring apparatus 200 may estimate bio-information of the object based on the measured optical signal in operation 1450. For example, the bio-signal measuring apparatus 200 may reconstruct a spectrum of the object based on the measured optical signal, and may estimate bio-information of the object by analyzing the reconstructed spectrum of the object. In this case, the bio-information may include blood pressure, vascular age, degree of arteriosclerosis, cardiac output, vascular compliance, blood glucose, triglyceride, cholesterol, protein, uric acid, peripheral vascular resistance, and the like.

Upon determining that the contact state is poor in operation 1440, the bio-signal measuring apparatus 200 may halt the operation of the optical sensor 210 and may stop measuring the optical signal by the optical sensor 210 until the bio-signal measuring apparatus 200 determines that the contact state between the object and the optical sensor 210 is good in operation 1460.

Figure 15:
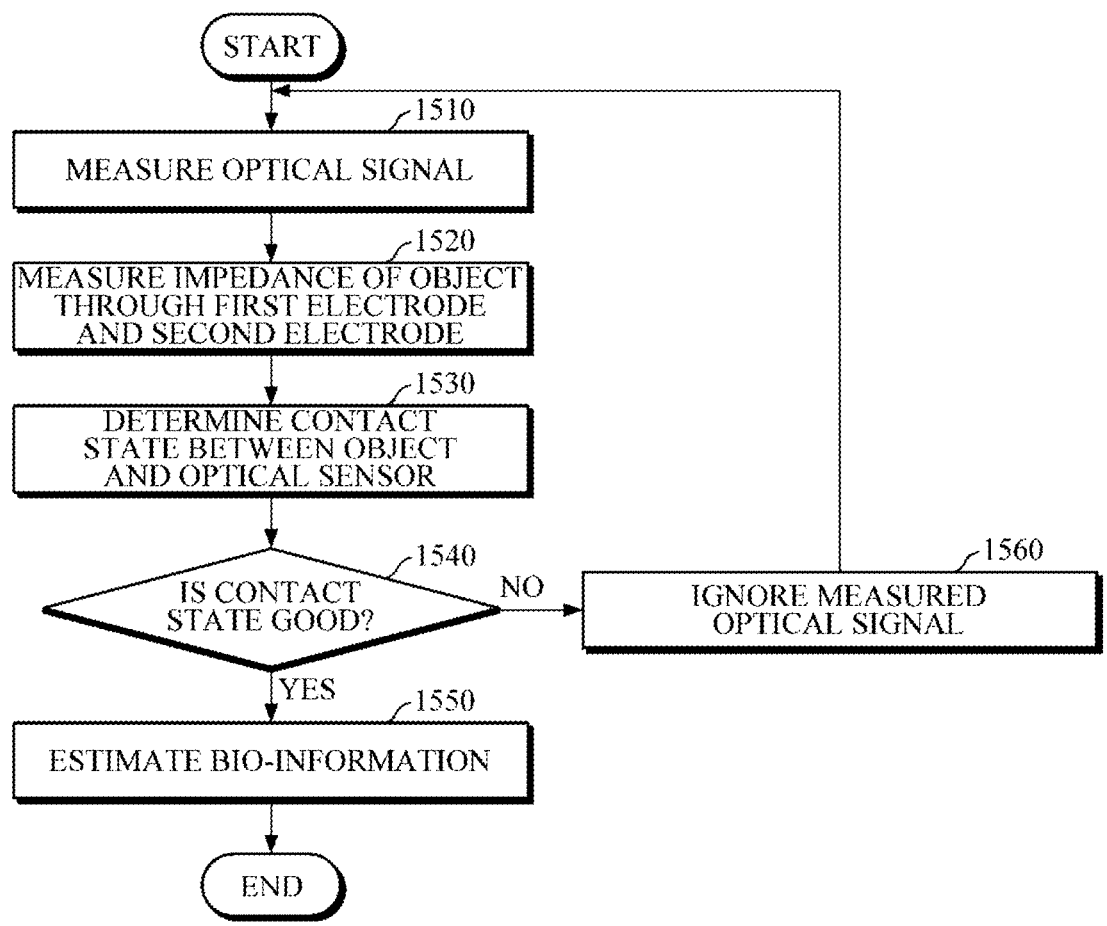
FIG. 15 is a flowchart illustrating another example of a bio-signal measuring method.

FIG. 15 is a flowchart illustrating another example of a bio-signal measuring method. The bio-signal measuring method of FIG. 15 may be performed by the bio-signal measuring apparatus 200 of FIG. 2.

Referring to FIGS. 2 and 15, the bio-signal measuring apparatus 200 may emit light onto an object by using the optical sensor 210, and may measure an optical signal of the object by receiving light reflected or scattered form the object in operation 1510.

The bio-signal measuring apparatus 200 may measure an impedance of the object through the first electrode 221 and the second electrode 222 in operation 1520.

The bio-signal measuring apparatus 200 may determine a contact state between the object and the optical sensor 210 based on the impedance of the object in operation 1530.

Upon determining that the contact state is good in operation 1540, the bio-signal measuring apparatus 200 may estimate bio-information of the object based on the measured optical signal in operation 1550.

Upon determining that the contact state is poor in operation 1540, the bio-signal measuring apparatus 200 may continue to measure the optical signal by the optical sensor 210, but may ignore an optical signal measured when the contact state is poor, and may not reflect the optical signal in analysis data in operation 1560.

Figure 16:
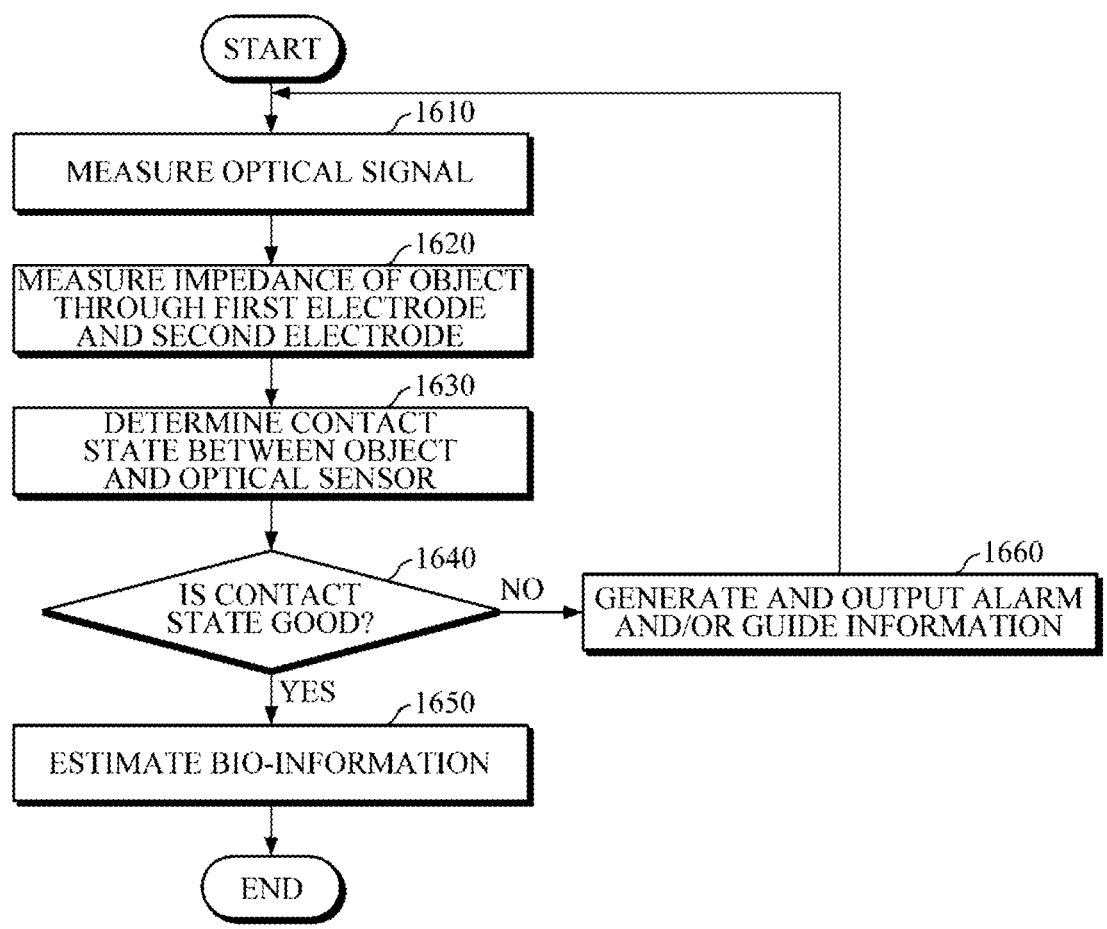
FIG. 16 is a flowchart illustrating yet another example of a bio-signal measuring method.

FIG. 16 is a flowchart illustrating yet another example of a bio-signal measuring method. The bio-signal measuring method of FIG. 16 may be performed by the bio-signal measuring apparatus 200 of FIG. 2.

Referring to FIGS. 2 and 16, the bio-signal measuring apparatus 200 may emit light onto an object by using the optical sensor 210, and may measure an optical signal of the object by receiving light reflected or scattered form the object in operation 1610.

The bio-signal measuring apparatus 200 may measure an impedance of the object through the first electrode 221 and the second electrode 222 in operation 1620.

The bio-signal measuring apparatus 200 may determine a contact state between the object and the optical sensor 210 based on the impedance of the object in operation 1630.

Upon determining that the contact state is good in operation 1640, the bio-signal measuring apparatus 200 may estimate bio-information of the object based on the measured optical signal in operation 1650.

Upon determining that the contact state is poor in operation 1640, the bio-signal measuring apparatus 200 may generate and output a predetermined alarm and/or guide information in operation 1660. In this case, the guide information may include information for inducing complete contact of the object with the optical sensor 210 to improve a contact state between the object and the optical sensor 210. For example, the guide information may include an image indicating which of the second electrodes has poor contact with the object, but is not limited thereto.

Figure 17:
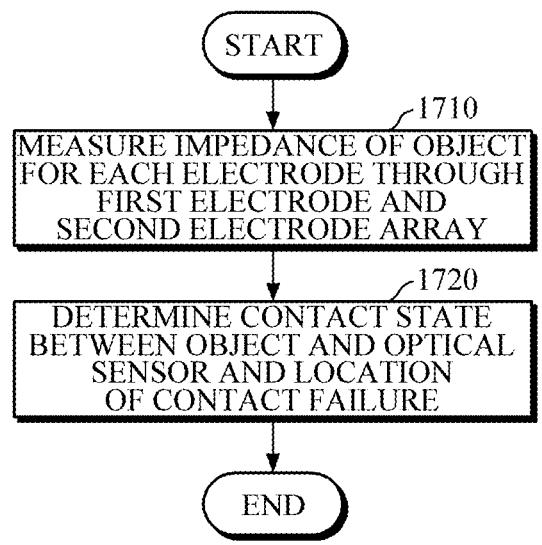
FIG. 17 is a flowchart illustrating another example of a method of determining a contact state.

FIG. 17 is a flowchart illustrating another example of a method of determining a contact state. The method of determining a contact state of FIG. 17 may be performed by the bio-signal measuring apparatus 700 of FIG. 7.

Referring to FIGS. 7 and 17, the bio-signal measuring apparatus 700 may measure an impedance of an object for each electrode through the first electrode 721 and the second electrode array 722 in operation 1710. In this case, an arrangement of the first electrode 721 and the second electrode array 722 is described above with reference to FIGS. 7 to 10, such that detailed description thereof will be omitted. In one embodiment, the bio-signal measuring apparatus 700 may apply a predetermined current to an object through the first electrode 721 and each second electrode of the second electrode array 722, may measure a voltage generated between the first electrode 721 and each second electrode by the applied current, and may obtain an impedance of the object for each electrode by using the relational expression (V=I*Z) among the voltage, the current, and the impedance based on the applied current and the measured voltage.

The bio-signal measuring apparatus 700 may determine a contact state between the object and the optical sensor 710 based on the measured impedance of the object for each electrode, and in case of a contact failure between the object and the optical sensor 710, the bio-signal measuring apparatus 700 may determine a location of the contact failure in operation 1720. For example, the bio-signal measuring apparatus 700 may compare each impedance of the object for each electrode with a predetermined threshold value; and in response to all the impedances of the object for each electrode being equal to or lower than the predetermined threshold value, the bio-signal measuring apparatus 700 may determine that the contact state between the object and the optical sensor 710 is good, and in response to one or more impedances for each electrode exceeding the predetermined threshold value, the bio-signal measuring apparatus 700 may determine that the contact state between the object and the optical sensor 710 is poor. In addition, the bio-signal measuring apparatus 700 may determine that the contact failure occurs in a direction of the second electrode where the impedance, which exceeds the predetermined threshold value, is measured.

Figure 18:
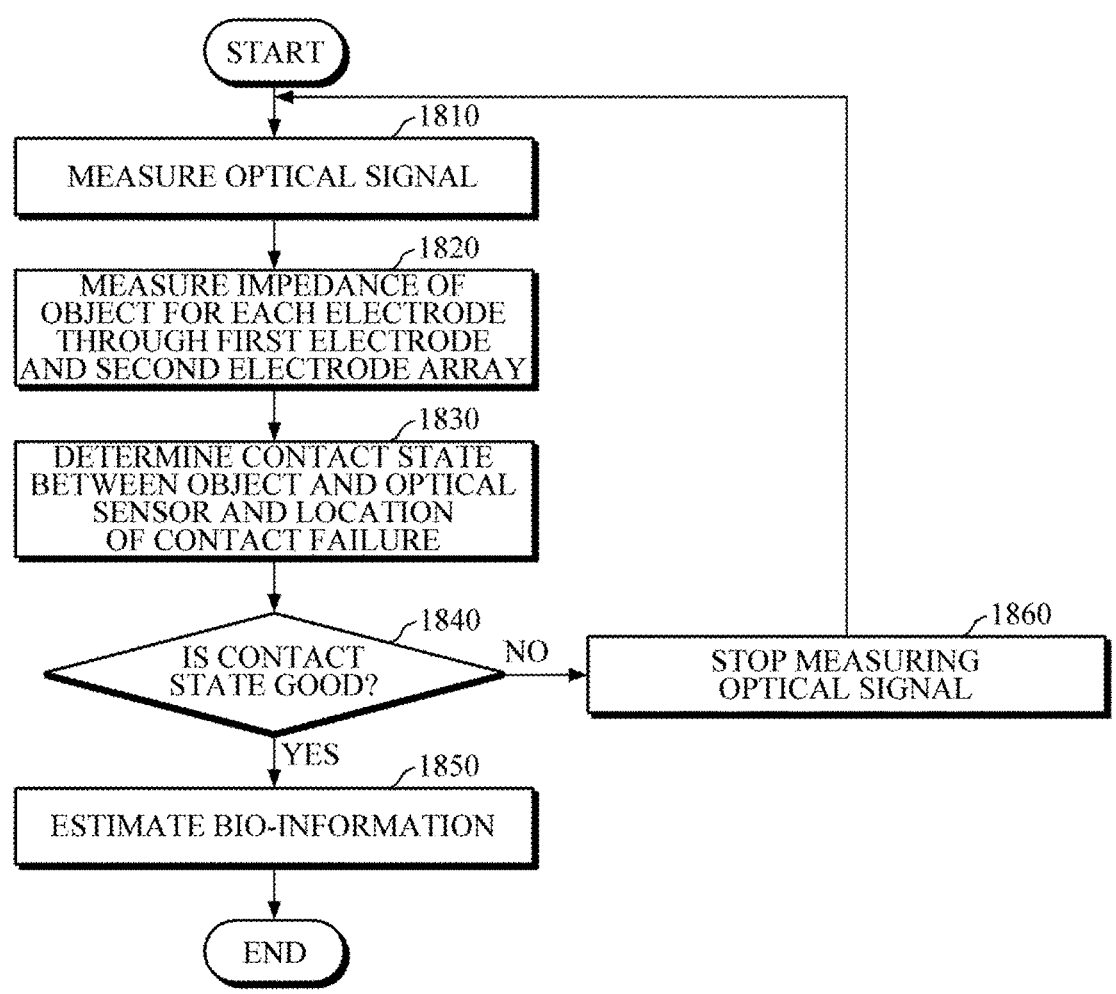
FIG. 18 is a flowchart illustrating yet another example of a bio-signal measuring method.

FIG. 18 is a flowchart illustrating still another example of a bio-signal measuring method. The bio-signal measuring method of FIG. 18 may be performed by the bio-signal measuring apparatus 700 of FIG. 7.

Referring to FIGS. 7 and 18, the bio-signal measuring apparatus 700 may emit light onto an object by using the optical sensor 710, and may measure an optical signal of the object by receiving light reflected or scattered form the object in operation 1810.

The bio-signal measuring apparatus 700 may measure an impedance of the object for each electrode through the first electrode 721 and the second electrode array 722 in operation 1820. In this case, an arrangement of the first electrode 721 and the second electrode array 722 is described above with reference to FIGS. 7 to 10, such that detailed description thereof will be omitted.

The bio-signal measuring apparatus 700 may determine a contact state between the object and the optical sensor 710 based on the measured impedance of the object for each electrode, and in case of a contact failure between the object and the optical sensor 710, the bio-signal measuring apparatus 700 may determine a location of the contact failure in operation 1830.

Upon determining that the contact state is good in operation 1840, the bio-signal measuring apparatus 700 may estimate bio-information of the object based on the measured optical signal in operation 1850. For example, the bio-signal measuring apparatus 700 may reconstruct a spectrum of the object based on the measured optical signal, and may estimate bio-information of the object by analyzing the reconstructed spectrum of the object. In this case, the bio-information may include blood pressure, vascular age, degree of arteriosclerosis, cardiac output, vascular compliance, blood glucose, triglyceride, cholesterol, protein, uric acid, peripheral vascular resistance, and the like.

Upon determining that the contact state is poor in operation 1840, the bio-signal measuring apparatus 700 may halt the operation of the optical sensor 710 and may stop measuring the optical signal by the optical sensor 710 in operation 1860 until the bio-signal measuring apparatus 700 determines that the contact state of the object with the optical sensor 710 is good.

Figure 19:
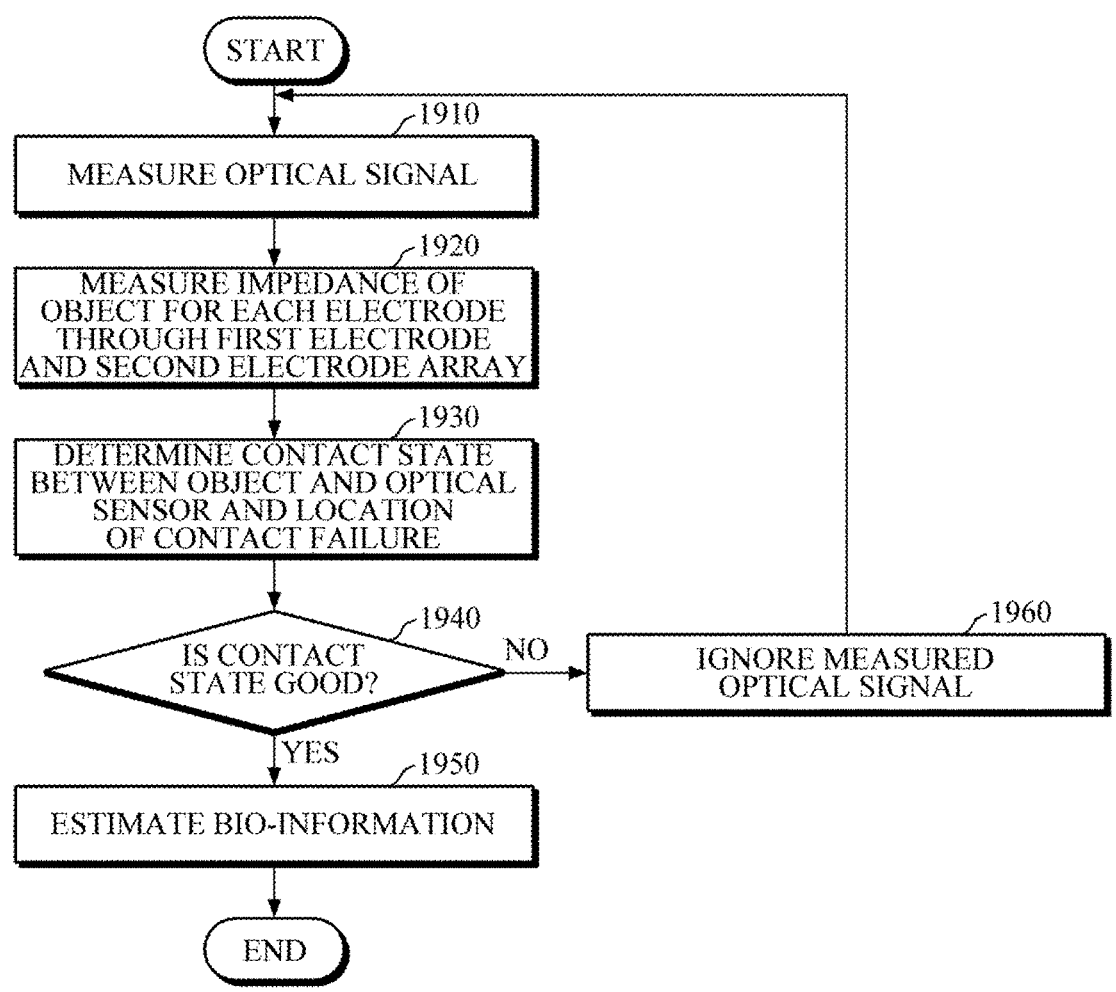
FIG. 19 is a flowchart illustrating still another example of a bio-signal measuring method.

FIG. 19 is a flowchart illustrating yet another example of a bio-signal measuring method. The bio-signal measuring method of FIG. 19 may be performed by the bio-signal measuring apparatus 700 of FIG. 7.

Referring to FIGS. 7 and 19, the bio-signal measuring apparatus 700 may emit light onto an object by using the optical sensor 710, and may measure an optical signal of the object by receiving light reflected or scattered form the object in operation 1910.

The bio-signal measuring apparatus 700 may measure an impedance of the object for each electrode through the first electrode 721 and the second electrode array 722 in operation 1920.

The bio-signal measuring apparatus 700 may determine a contact state between the object and the optical sensor 710 based on the measured impedance of the object for each electrode, and in case of a contact failure between the object and the optical sensor 710, the bio-signal measuring apparatus 700 may determine a location of the contact failure in operation 1930.

Upon determining that the contact state is good in operation 1940, the bio-signal measuring apparatus 700 may estimate bio-information of the object based on the measured optical signal in operation 1950.

Upon determining that the contact state is poor in operation 1940, the bio-signal measuring apparatus 700 may continue to measure the optical signal by the optical sensor 710, but may ignore an optical signal measured after being emitted from a light source in a location of the contact failure, and may not reflect the optical signal in analysis data in 1960.

Figure 20:
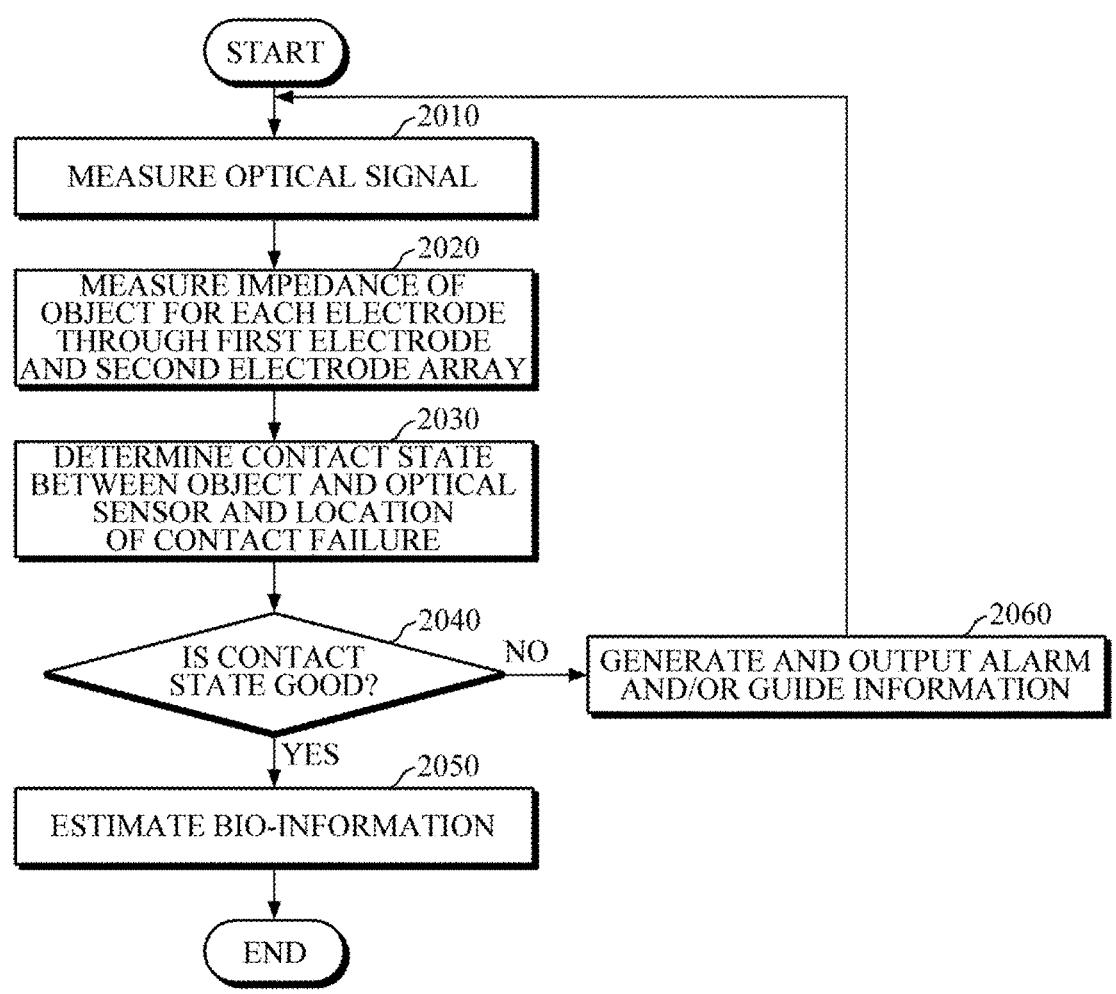
FIG. 20 is a flowchart illustrating still another example of a bio-signal measuring method.

FIG. 20 is a flowchart illustrating still another example of a bio-signal measuring method. The bio-signal measuring method of FIG. 20 may be performed by the bio-signal measuring apparatus 700 of FIG. 7.

Referring to FIGS. 7 and 20, the bio-signal measuring apparatus 700 may emit light onto an object by using the optical sensor 710, and may measure an optical signal of the object by receiving light reflected or scattered form the object in operation 2010.

The bio-signal measuring apparatus 700 may measure an impedance of the object for each electrode through the first electrode 721 and the second electrode array 722 in operation 2020.

The bio-signal measuring apparatus 700 may determine a contact state between the object and the optical sensor 710 based on the measured impedance of the object for each electrode, and in case of a contact failure between the object and the optical sensor 710, the bio-signal measuring apparatus 700 may determine a location of the contact failure in operation 2030.

Upon determining that the contact state is good in operation 2040, the bio-signal measuring apparatus 700 may estimate bio-information of the object based on the measured optical signal in operation 2050.

Upon determining that the contact state is poor in operation 2040, the bio-signal measuring apparatus 700 may generate and output a predetermined alarm and/or guide information in operation 2060. In this case, the guide information may include information for inducing complete contact of the object with the optical sensor 710 to improve a contact state between the object and the optical sensor 710.

Figure 21:
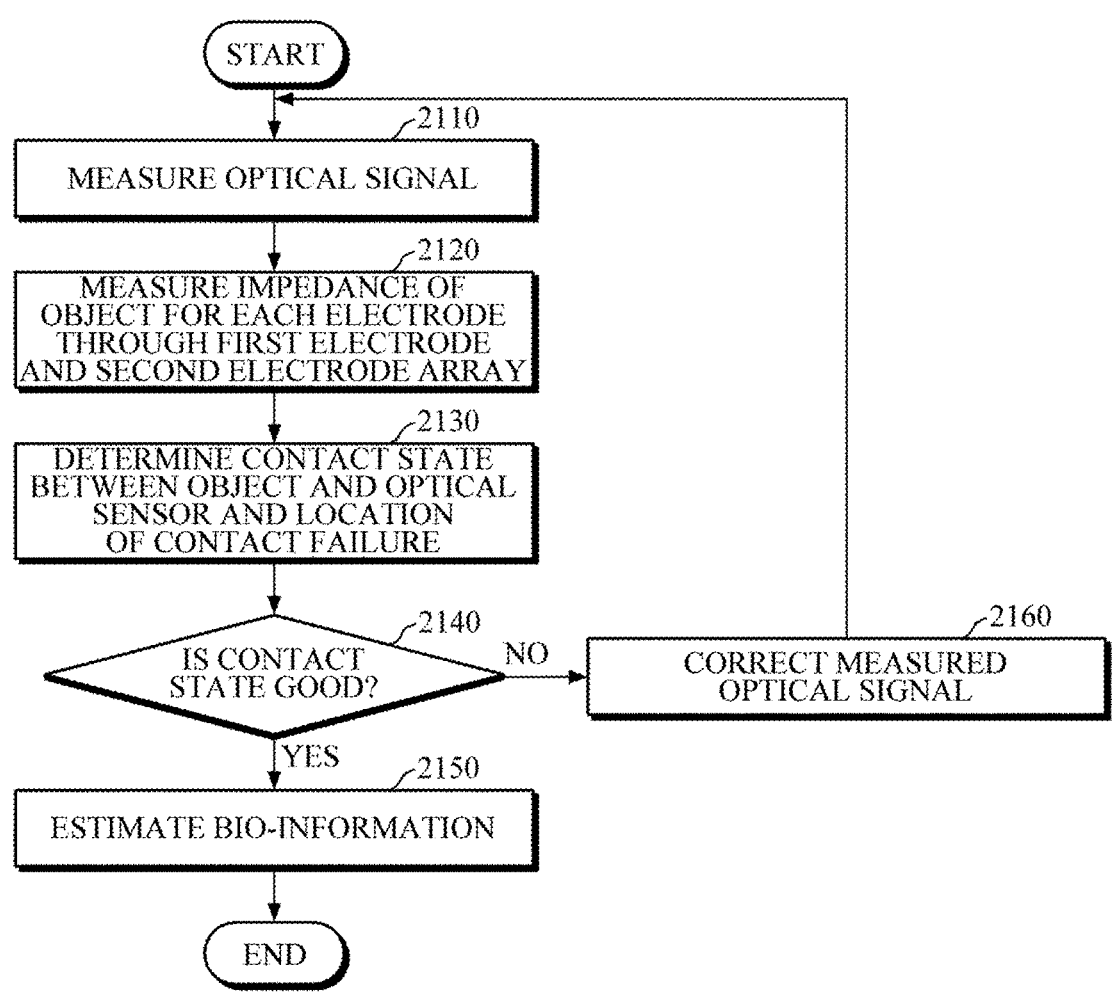
FIG. 21 is a flowchart illustrating still another example of a bio-signal measuring method.

FIG. 21 is a flowchart illustrating still another example of a bio-signal measuring method. The bio-signal measuring method of FIG. 21 may be performed by the bio-signal measuring apparatus 700 of FIG. 7.

Referring to FIGS. 7 and 21, the bio-signal measuring apparatus 700 may emit light onto an object by using the optical sensor 710, and may measure an optical signal of the object by receiving light reflected or scattered form the object in operation 2110.

The bio-signal measuring apparatus 700 may measure an impedance of the object for each electrode through the first electrode 721 and the second electrode array 722 in operation 2120.

The bio-signal measuring apparatus 700 may determine a contact state between the object and the optical sensor 710 based on the measured impedance of the object for each electrode, and in case of a contact failure between the object and the optical sensor 710, the bio-signal measuring apparatus 700 may determine a location of the contact failure in operation 2130.

Upon determining that the contact state is good in operation 2140, the bio-signal measuring apparatus 700 may estimate bio-information of the object based on the measured optical signal in operation 2150.

Upon determining that the contact state is poor in operation 2140, the bio-signal measuring apparatus 700 may correct the optical signal measured after being emitted from a light source in a location of the contact failure based on the impedance for each electrode in a location of the contact failure in operation 2160. In this case, the bio-signal measuring apparatus 700 may use a correction model that defines a relationship between impedance and an optical signal.

Figure 22:
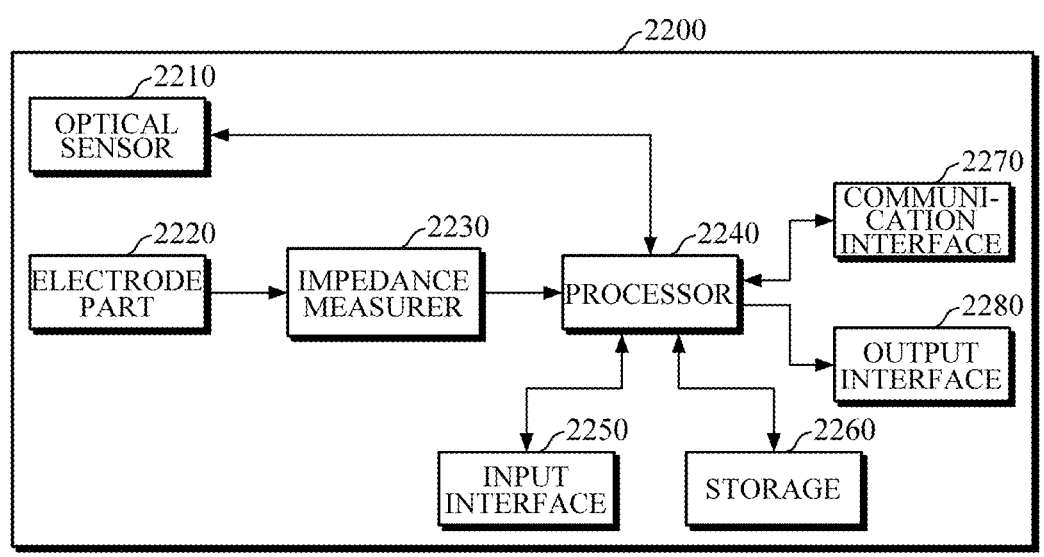
FIG. 22 is a block diagram illustrating yet another example of a bio-signal measuring apparatus.

FIG. 22 is a block diagram illustrating yet another example of a bio-signal measuring apparatus. A bio-signal measuring apparatus 2200 of FIG. 22 may be embedded in an external device. In this case, examples of the electronic device may include a cellular phone, a smartphone, a tablet PC, a laptop computer, a personal digital assistant (PDA), a portable multimedia player (PMP), a navigation, an MP3 player, a digital camera, a wearable device, and the like; and examples of the wearable device may include a watch-type wearable device, a wristband-type wearable device, a ring-type wearable device, a waist belt-type wearable device, a necklace-type wearable device, an ankle band-type wearable device, a thigh band-type wearable device, a forearm band-type wearable device, and the like. However, the electronic device is not limited thereto, and the wearable device is neither limited thereto.

Referring to FIG. 22, the bio-signal measuring apparatus 2200 includes an optical sensor 2210, an electrode part 2220, an impedance measurer 2230, a processor 2240, an input interface 2250, a storage 2260, a communication interface 2270, and an output interface 2280. Here, the optical sensor 2210, the electrode part 2220, the impedance measurer 2230, and the processor 2240 perform the same function as the optical sensors 210 and 710, the electrode parts 220 and 720, the impedance measurers 230 and 730, and the processors 240 and 740, such that detailed description thereof will be omitted.

The input interface 2250 may receive input of various operation signals from a user. In one embodiment, the input interface 2250 may include a keypad, a dome switch, a touch pad (static pressure/capacitance), a jog wheel, a jog switch, a hardware (H/W) button, and the like. The touch pad, which forms a layer structure with a display, may be called a touch screen.

The storage 2260 may store programs or instructions for operation of the bio-signal measuring apparatus 2200, and may store data input to and output from the bio-signal measuring apparatus 2200. Further, the storage 2260 may store the optical signal measured by the optical sensor 2210, the impedance of the object that is measured by the impedance measurer 2230, the determination of a contact state by the processor 2240, bio-information, guide information, and the like.

The storage 2260 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the bio-signal measuring apparatus 2200 may operate an external storage medium, such as web storage and the like, which performs a storage function of the storage 2260 on the Internet.

The communication interface 2270 may perform communication with an external device. For example, the communication interface 2270 may transmit the input data, the stored data, the processed data, and the like, which are stored in the bio-signal measuring apparatus 2200, to the external device, or may receive, from the external device, various data useful for determining a contact state and obtaining bio-information.

In this case, the external device may be medical equipment using the input data, the stored data, the processed data, and the like that are stored in the bio-signal measuring apparatus 2200, a printer to print out results, or a display to display the results. In addition, the external device may be a digital TV, a desktop computer, a cellular phone, a smartphone, a tablet PC, a laptop computer, a personal digital assistant (PDA), a portable multimedia player (PMP), a navigation, an MP3 player, a digital camera, a wearable device, and the like, but is not limited thereto.

The communication interface 2270 may communicate with an external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is an example and is not intended to be limiting.

The output interface 2280 may output data input from a user, the optical signal measured by the optical sensor 2210, the impedance of the object that is measured by the impedance measurer 2230, the determination of a contact state by the processor 2240, bio-information, guide information, and the like. In one embodiment, the output interface 2280 may output the data input from a user, the optical signal measured by the optical sensor 2210, the impedance of the object that is measured by the impedance measurer 2230, the determination of a contact state by the processor 2240, the bio-information, the guide information, and the like by using any one or any combination of an acoustic method, a visual method, and a tactile method. To this end, the output interface 2280 may include a display, a speaker, a vibrator, and the like.

Figure 23:
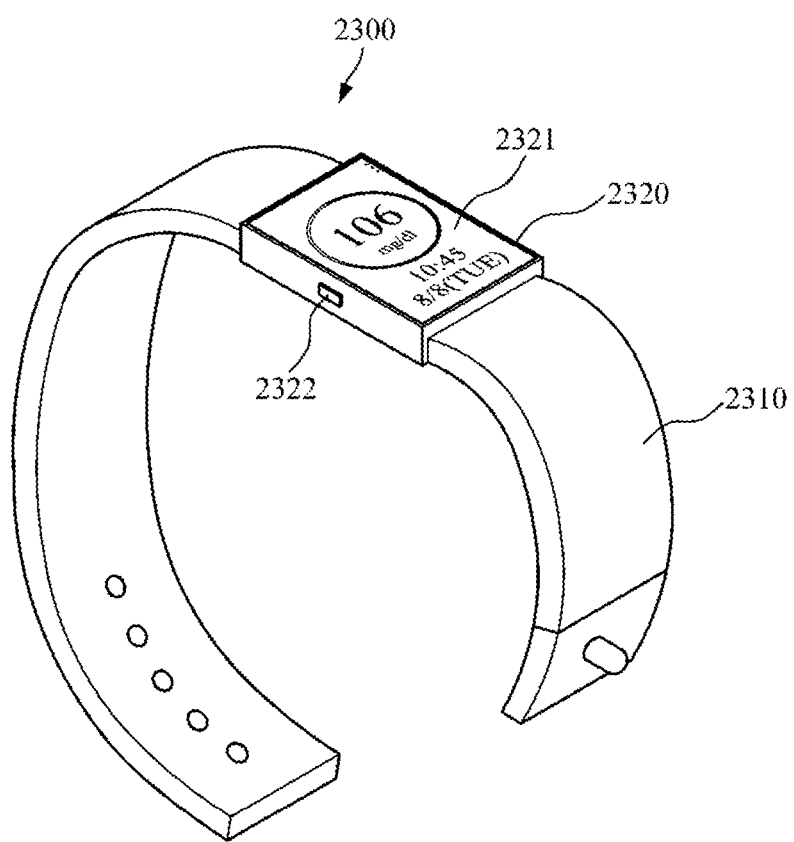
FIG. 23 is a diagram illustrating a wrist-type wearable device.

FIG. 23 is a diagram illustrating a wrist-type wearable device.

Referring to FIG. 23, a wrist-type wearable device 2300 includes a strap 2310 and a main body 2320.

The strap 2310 may be connected at both sides of the main body 2320, and may be fastened to each other in a detachable manner, or may be integrally formed as a smart band strap. The strap 2310 may be made of a flexible material to wrap around a user's wrist so that the main body 2320 may be worn around a user's wrist.

The main body 2320 may include the above-described bio-signal measuring apparatuses 200, 700, and 2200. Further, the main body 2320 may include a battery that supplies power to the wrist-type wearable device 2300 and the bio-signal measuring apparatuses 200, 700, and 2200.

The optical sensor and the electrode may be mounted at the bottom of the main body 2330 to be exposed to the wrist of a user. In this manner, when a user wears the wrist-type wearable device 2300, the light sensor may naturally come into contact with a user's skin.

The wrist-type wearable device 2300 may further include a display 2321 and an input interface 2322 that are mounted in the main body 2320. The display 2321 may display data processed by the wrist-type wearable device 2300 and the bio-signal measuring apparatuses 200, 700, and 2200, processing result data, and the like thereof. The input interface 2322 may receive input of various operation signals from a user.

The disclosure can be realized as a computer-readable code written on a computer-readable recording medium. Codes and code segments for realizing the disclosure can be easily deduced by computer programmers of ordinary skill in the art. The computer-readable recording medium may be any type of recording device in which data is stored in a computer-readable manner. Examples of the computer-readable recording medium include a ROM, a RAM, a CD-ROM, a magnetic tape, a floppy disc, an optical disk, and the like. Further, the computer-readable recording medium can be distributed over a plurality of computer systems connected to a network so that a computer-readable recording medium is written thereto and executed therefrom in a decentralized manner.

The inventive concept has been described herein with regard to embodiments. However, it will be obvious to those skilled in the art that various modifications can be made without departing from the gist of the inventive concept. Therefore, it is to be understood that that the scope of the inventive concept is not limited to the above-mentioned embodiments, but is intended to include various modifications and equivalents included within the spirit and scope of the appended claims.

What is claimed is:

1. A bio-signal measuring apparatus, comprising:
an optical sensor configured to measure an optical signal, the optical sensor comprising:
a housing;
a photodetector; and
a light source array disposed around the photodetector, wherein the photodetector and the light source array being mounted on or around the housing;
a first electrode disposed between the photodetector and the light source array;
a second electrode array disposed on an outer periphery of the light source array, the second electrode array comprising a plurality of electrodes that are separate from each other;
an impedance measurer configured to measure an impedance of an object for each of the plurality of electrodes, using the first electrode and the second electrode array; and
a processor configured to:
determine a contact state between the object and the optical sensor, and a location of a contact failure between the object and the optical sensor, based on the measured impedance for each of the plurality of electrodes; and
perform any one or any combination of controlling the optical sensor to stop measuring the optical signal and ignoring the measured optical signal, based on the contact state being determined to be poor,
wherein the optical sensor further comprises respective pairs of direction adjusters that are accommodated within the housing of the optical sensor, the respective pairs of direction adjusters being configured to adjust a direction of light emitted by the light source array to be directed toward a portion to be examined of the object, and
wherein light sources included in the light source array are positioned between a corresponding pair of direction adjusters.

2. The apparatus of claim 1, wherein each of the first electrode and the second electrode array has a ring shape.

3. The apparatus of claim 2, wherein each of the first electrode and the second electrode array has a concentric ring shape.

4. The apparatus of claim 1, wherein the impedance measurer is further configured to:
apply a current to the object, through the first electrode and each of the plurality of electrodes;
measure a voltage that is generated between the first electrode and each of the plurality of electrodes through which the current is applied to the object; and
obtain the impedance for each of the plurality of electrodes, based on the applied current and the measured voltage generated between the first electrode and each of the plurality of electrodes.

5. The apparatus of claim 1, wherein the processor is further configured to:
compare the measured impedance for each of the plurality of electrodes, with a predetermined threshold value; and
determine the contact state and the location of the contact failure, based on a result of the measured impedance for each of the plurality of electrodes being compared with the predetermined threshold value.

6. The apparatus of claim 5, wherein the processor is further configured to, based on the measured impedance for each of the plurality of electrodes being compared to be less than or equal to the predetermined threshold value, determine that the contact state is good.

7. The apparatus of claim 6, wherein the processor is further configured to, based on the contact state being determined to be good, estimate bio-information of the object, using the measured optical signal.

8. The apparatus of claim 7, wherein the bio-information comprises any one or any combination of a blood pressure, a vascular age, a degree of arteriosclerosis, a cardiac output, a vascular compliance, a blood glucose, a triglyceride, a cholesterol, a protein, an uric acid, and a peripheral vascular resistance.

9. The apparatus of claim 5, wherein the processor is further configured to:
based on the measured impedance for at least one of the plurality of electrodes being compared to be greater than the predetermined threshold value, determine that the contact state is poor; and
determine the location of the contact failure at the at least one of the plurality of electrodes for which the measured impedance is greater than the predetermined threshold value.

10. The apparatus of claim 1, wherein the optical sensor further comprises a light concentrator configured to concentrate light, which is reflected or scattered from the object, to be directed toward the photodetector.

11. The apparatus of claim 1, wherein the optical sensor further comprises wavelength adjusters provided on or around the light sources included in the light source array, the wavelength adjusters being configured to control the light sources to emit light of a predetermined peak wavelength range.

12. An operating method of a bio-signal measuring apparatus that comprises an optical sensor comprising a photodetector and a light source array disposed around the photodetector; a first electrode disposed between the photodetector and the light source array; a second electrode array disposed on an outer periphery of the light source array, the second electrode array comprising a plurality of electrodes that are separate from each other; an impedance measurer; and a processor, wherein the optical sensor further comprises a housing, and the photodetector and the light source array are mounted on or around the housing, the method comprising:
measuring, by using the optical sensor, an optical signal;
measuring, by using the impedance measurer, an impedance of an object for each of the plurality of electrodes, using the first electrode and the second electrode array;
determining, by using the processor, a contact state between the object and the optical sensor, and a location of a contact failure between the object and the optical sensor, based on the measured impedance for each of the plurality of electrodes; and
performing, by using the processor, any one or any combination of controlling the optical sensor to stop measuring the optical signal and ignoring the measured optical signal, based on the contact state being determined to be poor, wherein the optical sensor further comprises respective pairs of direction adjusters that are accommodated within the housing of the optical sensor, and light sources included in the light source array are positioned between a corresponding pair of direction adjusters, and wherein the method further comprises adjusting, by using the respective pairs of direction adjusters, a direction of light emitted by the light source array to be directed toward a portion to be examined of the object.

13. The method of claim 12, wherein the measuring of the impedance comprises:

applying a current to the object, through the first electrode and each of the plurality of electrodes;

measuring a voltage that is generated between the first electrode and each of the plurality of electrodes through which the current is applied to the object; and obtaining the impedance for each of the plurality of electrodes, based on the applied current and the measured voltage generated between the first electrode and each of the plurality of electrodes.

14. The method of claim 12, wherein the determining of the contact state comprises:

comparing the measured impedance for each of the plurality of electrodes, with a predetermined threshold value; and determining the contact state and the location of the contact failure, based on a result of the measured impedance for each of the plurality of electrodes being compared with the predetermined threshold value.

15. The method of claim 14, wherein the determining of the contact state further comprises, based on the measured impedance for each of the plurality of electrodes being compared to be less than or equal to the predetermined threshold value, determining that the contact state is good.

16. The method of claim 15, further comprising, based on the contact state being determined to be good, estimating bio-information of the object, using the measured optical signal.

17. The method of claim 16, wherein the bio-information comprises any one or any combination of a blood pressure, a vascular age, a degree of arteriosclerosis, a cardiac output, a vascular compliance, a blood glucose, a triglyceride, a cholesterol, a protein, an uric acid, and a peripheral vascular resistance.

18. The method of claim 14, wherein the determining of the contact state and the location of the contact failure further comprises:

based on the measured impedance being compared to be greater than the predetermined threshold value, determining that the contact state is poor; and determining the location of the contact failure at the at least one of the plurality of electrodes for which the measured impedance is greater than the predetermined threshold value.

* * * * *